(12) United States Patent
Reynolds et al.

(10) Patent No.: US 8,765,144 B2
(45) Date of Patent: Jul. 1, 2014

(54) **ANTIGENIC COMPLEX FOR THE DIAGNOSIS AND TREATMENT OF *PORPHYROMONAS GINGIVALIS* INFECTION**

(75) Inventors: Eric Charles Reynolds, Balwyn (AU); Neil Martin O'Brien-Simpson, Brunswick (AU); Rishi Delan Pathirana, Keysborough (AU)

(73) Assignee: The University of Melbourne, Parkville, Victoria (AU)

( * ) Notice: Subject to any disclaimer, the term of this patent is extended or adjusted under 35 U.S.C. 154(b) by 513 days.

(21) Appl. No.: 12/944,399

(22) Filed: Nov. 11, 2010

(65) Prior Publication Data

US 2011/0081358 A1    Apr. 7, 2011

Related U.S. Application Data

(63) Continuation of application No. 11/663,671, filed as application No. PCT/AU2005/001463 on Sep. 23, 2005, now abandoned.

(30) Foreign Application Priority Data

Sep. 23, 2004  (AU) ................................ 2004905478

(51) Int. Cl.
*A61K 39/02* (2006.01)
(52) U.S. Cl.
USPC ...................................... 424/234.1; 424/94.2
(58) Field of Classification Search
None
See application file for complete search history.

(56) References Cited

U.S. PATENT DOCUMENTS 6,511,666 B1 *  1/2003 Reynolds et al. .......... 424/184.1
2002/0164759 A1 * 11/2002 Travis et al. ................. 435/219

FOREIGN PATENT DOCUMENTS

WO    WO 97/165542 A1    5/1997

OTHER PUBLICATIONS

Bhogal et al (Microbiology, 143(7):2485-2495, 1997).*
Pathirana et al (Microbiology, 152(8):2381-2394, 2006).*
BIO Critical Synergy: The Biotechnology Industry and Intellectual Property Protection, Biotechnology Industry Organization, Presentations Oct. 17, 1994, pp. 100-107.*
Sigma Catalog, 2002-2003, p. 2090-2091.*
Zeitlin et al (Emerging Infectious Diseases, 5:54-64, 1999).*
Yixin Shi et al., "Genetic Analysis of Proteolysis, Hemoglobin Binding, and Hemagglutination of *Porphyromonas gingivalis*", The Journal of Biological Chemistry, vol. 274, No. 25, Issue of Jun. 18, 1999, pp. 17955-17960.
Rajapakse et al., "Immunization with RgpA-Kgp Proteinase-Adhesin Complexes of *Porphyromonas gingivalis* Protects against Periodontal Bone Loss in the Rat Periodontitis Model," Infection and Immunity, vol. 70, No. 5, pp. 2480-2486, May 2002.
International Search Report issued in application No. PCT/AU2005/001463 on Nov. 1, 2005.
Pike et al., "Lysine- and Arginine-specific Proteinases from *Porphyromonas gingivalis,*" The Journal of Biological Chemistry, vol. 269, No. 1, pp. 406-411, Jan. 7, 1984.
Bhogal et al., "A cell-associated protein complex of *Porphyromonas gingivalis* W50 composed of Arg- and Lys-specific cysteine proteinases and adhesins," Microbiology, vol. 143, pp. 2485-2495, 1997.
O'Brien-Simpson et al., "RgpA-Kgp Peptide-Based Immunogens Provide Protection against *Porphyrumonas gingivalis* Challenge in a Murine Lesion Model," Infection and Immunity, vol. 68, No. 7, pp. 4055-4063, Jul. 2000.
Sigma, "TRITON™X-100," Sigma catalog issued 2002-2003, pp. 2090-2091.
Office Action issued on May 12, 2010 in U.S. Appl. No. 11/663,671 (US 2009/0169568).
Office Action issued on Nov. 4, 2009 in U.S. Appl. No. 11/663,671 (US 2009/0169588).

* cited by examiner

*Primary Examiner* — Patricia A Duffy
(74) *Attorney, Agent, or Firm* — Foley & Lardnder LLP

(57) ABSTRACT

The present invention provides a purified multimeric complex from *P. gingivalis*. The complex comprises at least one domain from each of RgpA, Kgp and HagA, and has a molecular weight greater than about 300 kDa.

9 Claims, 8 Drawing Sheets

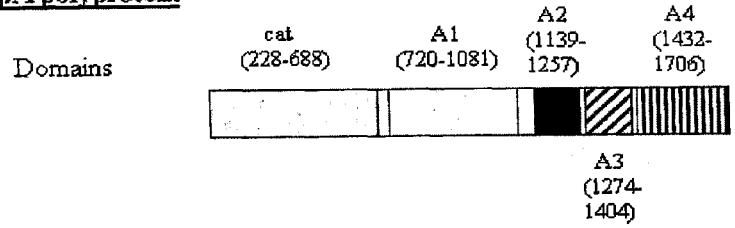

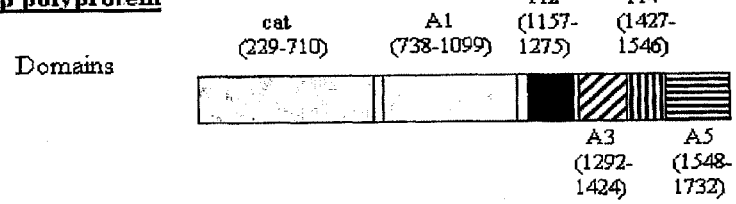

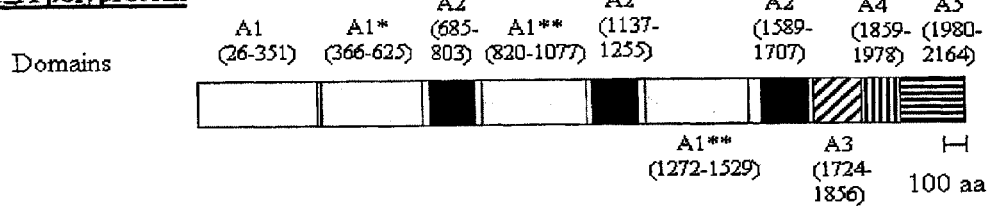

N-terminal sequence of the processed domains of RgpA, Kgp and HagA

RgpA polyprotein
- RgpA$_{cat}$ YTPVEEKQ (SEQ ID No:60)
- RgpA$_{A1}$ SGQAEIVL (SEQ ID No:61)
- RgpA$_{A2}$ ADFTETFE (SEQ ID No:62)
- RgpA$_{A3}$ PQSVWIER (SEQ ID No:54)
- RgpA$_{A4}$ ANEAKVVL (SEQ ID No:63)

Kgp polyprotein
- Kgp$_{cat}$ DVYTDHGD (SEQ ID No:64)
- Kgp$_{A1}$ ANEAKVVL (SEQ ID No:63)
- Kgp$_{A2}$ ADFTETFE (SEQ ID No:62)
- Kgp$_{A3}$ PQSVWIER (SEQ ID No:54)
- Kgp$_{A4}$ AEVLNEDF (SEQ ID No:65)
- Kgp$_{A5}$ TVVTAPEA (SEQ ID No:66)

HagA polyprotein
- HagA$_{A1}$ GGPKTAPS (SEQ ID No:67)
- HagA$_{A1*}$ APAPYQER (SEQ ID No:68)
- HagA$_{A1**}$ PQSVWIER (SEQ ID No:54)
- HagA$_{A2}$ ADFTETFE (SEQ ID No:62)
- HagA$_{A3}$ PQSVWIER (SEQ ID No:54)
- HagA$_{A4}$ AELLNEDF (SEQ ID No:69)
- HagA$_{A5}$ TVVTAPE (SEQ ID No:70)

Figure 3.

SEQUENCE LISTING

```
<160> NUMBER OF SEQ ID NOS: 70

<210> SEQ ID NO 1
<211> LENGTH: 1706
<212> TYPE: PRT
<213> ORGANISM: Porphyromonas gingivalis

<400> SEQUENCE: 1

Met Lys Asn Leu Asn Lys Phe Val Ser Ile Ala Leu Cys Ser Ser Leu
 1               5                  10                  15
```

-continued

```
Leu Gly Gly Met Ala Phe Ala Gln Gln Thr Glu Leu Gly Arg Asn Pro
             20                  25                  30

Asn Val Arg Leu Leu Glu Ser Thr Gln Gln Ser Val Thr Lys Val Gln
         35                  40                  45

Phe Arg Met Asp Asn Leu Lys Phe Thr Glu Val Gln Thr Pro Lys Gly
     50                  55                  60

Ile Gly Gln Val Pro Thr Tyr Thr Glu Gly Val Asn Leu Ser Glu Lys
65                  70                  75                  80

Gly Met Pro Thr Leu Pro Ile Leu Ser Arg Ser Leu Ala Val Ser Asp
                 85                  90                  95

Thr Arg Glu Met Lys Val Glu Val Val Ser Ser Lys Phe Ile Glu Lys
            100                 105                 110

Lys Asn Val Leu Ile Ala Pro Ser Lys Gly Met Ile Met Arg Asn Glu
        115                 120                 125

Asp Pro Lys Lys Ile Pro Tyr Val Tyr Gly Lys Thr Tyr Ser Gln Asn
    130                 135                 140

Lys Phe Phe Pro Gly Glu Ile Ala Thr Leu Asp Asp Pro Phe Ile Leu
145                 150                 155                 160

Arg Asp Val Arg Gly Gln Val Val Asn Phe Ala Pro Leu Gln Tyr Asn
                165                 170                 175

Pro Val Thr Lys Thr Leu Arg Ile Tyr Thr Glu Ile Thr Val Ala Val
            180                 185                 190

Ser Glu Thr Ser Glu Gln Gly Lys Asn Ile Leu Asn Lys Lys Gly Thr
        195                 200                 205

Phe Ala Gly Phe Glu Asp Thr Tyr Lys Arg Met Phe Met Asn Tyr Glu
    210                 215                 220

Pro Gly Arg Tyr Thr Pro Val Glu Glu Lys Gln Asn Gly Arg Met Ile
225                 230                 235                 240

Val Ile Val Ala Lys Lys Tyr Glu Gly Asp Ile Lys Asp Phe Val Asp
                245                 250                 255

Trp Lys Asn Gln Arg Gly Leu Arg Thr Glu Val Lys Val Ala Glu Asp
            260                 265                 270

Ile Ala Ser Pro Val Thr Ala Asn Ala Ile Gln Gln Phe Val Lys Gln
        275                 280                 285

Glu Tyr Glu Lys Glu Gly Asn Asp Leu Thr Tyr Val Leu Leu Ile Gly
    290                 295                 300

Asp His Lys Asp Ile Pro Ala Lys Ile Thr Pro Gly Ile Lys Ser Asp
305                 310                 315                 320

Gln Val Tyr Gly Gln Ile Val Gly Asn Asp His Tyr Asn Glu Val Phe
                325                 330                 335

Ile Gly Arg Phe Ser Cys Glu Ser Lys Glu Asp Leu Lys Thr Gln Ile
            340                 345                 350

Asp Arg Thr Ile His Tyr Glu Arg Asn Ile Thr Thr Glu Asp Lys Trp
        355                 360                 365

Leu Gly Gln Ala Leu Cys Ile Ala Ser Ala Glu Gly Gly Pro Ser Ala
    370                 375                 380

Asp Asn Gly Glu Ser Asp Ile Gln His Glu Asn Val Ile Ala Asn Leu
385                 390                 395                 400

Leu Thr Gln Tyr Gly Tyr Thr Lys Ile Ile Lys Cys Tyr Asp Pro Gly
                405                 410                 415

Val Thr Pro Lys Asn Ile Ile Asp Ala Phe Asn Gly Ile Ser Leu
            420                 425                 430

Ala Asn Tyr Thr Gly His Gly Ser Glu Thr Ala Trp Gly Thr Ser His
```

-continued

```
            435                 440                 445
Phe Gly Thr Thr His Val Lys Gln Leu Thr Asn Ser Asn Gln Leu Pro
450                 455                 460
Phe Ile Phe Asp Val Ala Cys Val Asn Gly Asp Phe Leu Phe Ser Met
465                 470                 475                 480
Pro Cys Phe Ala Glu Ala Leu Met Arg Ala Gln Lys Asp Gly Lys Pro
                485                 490                 495
Thr Gly Thr Val Ala Ile Ile Ala Ser Thr Ile Asn Gln Ser Trp Ala
                500                 505                 510
Ser Pro Met Arg Gly Gln Asp Glu Met Asn Glu Ile Leu Cys Glu Lys
            515                 520                 525
His Pro Asn Asn Ile Lys Arg Thr Phe Gly Gly Val Thr Met Asn Gly
            530                 535                 540
Met Phe Ala Met Val Glu Lys Tyr Lys Lys Asp Gly Glu Lys Met Leu
545                 550                 555                 560
Asp Thr Trp Thr Val Phe Gly Asp Pro Ser Leu Leu Val Arg Thr Leu
                565                 570                 575
Val Pro Thr Lys Met Gln Val Thr Ala Pro Ala Gln Ile Asn Leu Thr
            580                 585                 590
Asp Ala Ser Val Asn Val Ser Cys Asp Tyr Asn Gly Ala Ile Ala Thr
            595                 600                 605
Ile Ser Ala Asn Gly Lys Met Phe Gly Ser Ala Val Val Glu Asn Gly
610                 615                 620
Thr Ala Thr Ile Asn Leu Thr Gly Leu Thr Asn Glu Ser Thr Leu Thr
625                 630                 635                 640
Leu Thr Val Val Gly Tyr Asn Lys Glu Thr Val Ile Lys Thr Ile Asn
                645                 650                 655
Thr Asn Gly Glu Pro Asn Pro Tyr Gln Pro Val Ser Asn Leu Thr Ala
                660                 665                 670
Thr Thr Gln Gly Gln Lys Val Thr Leu Lys Trp Asp Ala Pro Ser Thr
            675                 680                 685
Lys Thr Asn Ala Thr Thr Asn Thr Ala Arg Ser Val Asp Gly Ile Arg
            690                 695                 700
Glu Leu Val Leu Leu Ser Val Ser Asp Ala Pro Glu Leu Leu Arg Ser
705                 710                 715                 720
Gly Gln Ala Glu Ile Val Leu Glu Ala His Asp Val Trp Asn Asp Gly
                725                 730                 735
Ser Gly Tyr Gln Ile Leu Leu Asp Ala Asp His Asp Gln Tyr Gly Gln
                740                 745                 750
Val Ile Pro Ser Asp Thr His Thr Leu Trp Pro Asn Cys Ser Val Pro
            755                 760                 765
Ala Asn Leu Phe Ala Pro Phe Glu Tyr Thr Val Pro Glu Asn Ala Asp
            770                 775                 780
Pro Ser Cys Ser Pro Thr Asn Met Ile Met Asp Gly Thr Ala Ser Val
785                 790                 795                 800
Asn Ile Pro Ala Gly Thr Tyr Asp Phe Ala Ile Ala Ala Pro Gln Ala
                805                 810                 815
Asn Ala Lys Ile Trp Ile Ala Gly Gln Gly Pro Thr Lys Glu Asp Asp
                820                 825                 830
Tyr Val Phe Glu Ala Gly Lys Lys Tyr His Phe Leu Met Lys Lys Met
            835                 840                 845
Gly Ser Gly Asp Gly Thr Glu Leu Thr Ile Ser Glu Gly Gly Gly Ser
850                 855                 860
```

-continued

```
Asp Tyr Thr Tyr Thr Val Tyr Arg Asp Gly Lys Ile Lys Glu Gly
865                 870                 875                 880

Leu Thr Ala Thr Thr Phe Glu Glu Asp Gly Val Ala Thr Gly Asn His
            885                 890                 895

Glu Tyr Cys Val Glu Val Lys Tyr Thr Ala Gly Val Ser Pro Lys Val
        900                 905                 910

Cys Lys Asp Val Thr Val Glu Gly Ser Asn Glu Phe Ala Pro Val Gln
            915                 920                 925

Asn Leu Thr Gly Ser Ala Val Gly Gln Lys Val Thr Leu Lys Trp Asp
930                 935                 940

Ala Pro Asn Gly Thr Pro Asn Pro Asn Pro Asn Pro Asn Pro Asn Pro
945                 950                 955                 960

Asn Pro Gly Thr Thr Thr Leu Ser Glu Ser Phe Glu Asn Gly Ile Pro
            965                 970                 975

Ala Ser Trp Lys Thr Ile Asp Ala Asp Gly Asp Gly His Gly Trp Lys
            980                 985                 990

Pro Gly Asn Ala Pro Gly Ile Ala Gly Tyr Asn Ser Asn Gly Cys Val
        995                 1000                1005

Tyr Ser Glu Ser Phe Gly Leu Gly Gly Ile Gly Val Leu Thr Pro Asp
    1010                1015                1020

Asn Tyr Leu Ile Thr Pro Ala Leu Asp Leu Pro Asn Gly Gly Lys Leu
1025                1030                1035                1040

Thr Phe Trp Val Cys Ala Gln Asp Ala Asn Tyr Ala Ser Glu His Tyr
            1045                1050                1055

Ala Val Tyr Ala Ser Ser Thr Gly Asn Asp Ala Ser Asn Phe Thr Asn
    1060                1065                1070

Ala Leu Leu Glu Glu Thr Ile Thr Ala Lys Gly Val Arg Ser Pro Glu
    1075                1080                1085

Ala Met Arg Gly Arg Ile Gln Gly Thr Trp Arg Gln Lys Thr Val Asp
    1090                1095                1100

Leu Pro Ala Gly Thr Lys Tyr Val Ala Phe Arg His Phe Gln Ser Thr
1105                1110                1115                1120

Asp Met Phe Tyr Ile Asp Leu Asp Glu Val Glu Ile Lys Ala Asn Gly
            1125                1130                1135

Lys Arg Ala Asp Phe Thr Glu Thr Phe Glu Ser Ser Thr His Gly Glu
            1140                1145                1150

Ala Pro Ala Glu Trp Thr Thr Ile Asp Ala Asp Gly Asp Gly Gln Gly
            1155                1160                1165

Trp Leu Cys Leu Ser Ser Gly Gln Leu Asp Trp Leu Thr Ala His Gly
            1170                1175                1180

Gly Thr Asn Val Val Ser Ser Phe Ser Trp Asn Gly Met Ala Leu Asn
1185                1190                1195                1200

Pro Asp Asn Tyr Leu Ile Ser Lys Asp Val Thr Gly Ala Thr Lys Val
            1205                1210                1215

Lys Tyr Tyr Ala Val Asn Asp Gly Phe Pro Gly Asp His Tyr Ala
            1220                1225                1230

Val Met Ile Ser Lys Thr Gly Thr Asn Ala Gly Asp Phe Thr Val Val
            1235                1240                1245

Phe Glu Glu Thr Pro Asn Gly Ile Asn Lys Gly Gly Ala Arg Phe Gly
            1250                1255                1260

Leu Ser Thr Glu Ala Asp Gly Ala Lys Pro Gln Ser Val Trp Ile Glu
1265                1270                1275                1280
```

```
Arg Thr Val Asp Leu Pro Ala Gly Thr Lys Tyr Val Ala Phe Arg His
            1285                1290                1295

Tyr Asn Cys Ser Asp Leu Asn Tyr Ile Leu Leu Asp Asp Ile Gln Phe
        1300                1305                1310

Thr Met Gly Gly Ser Pro Thr Pro Thr Asp Tyr Thr Tyr Thr Val Tyr
        1315                1320                1325

Arg Asp Gly Thr Lys Ile Lys Glu Gly Leu Thr Glu Thr Thr Phe Glu
        1330                1335                1340

Glu Asp Gly Val Ala Thr Gly Asn His Glu Tyr Cys Val Glu Val Lys
1345                1350                1355                1360

Tyr Thr Ala Gly Val Ser Pro Lys Lys Cys Val Asn Val Thr Val Asn
            1365                1370                1375

Ser Thr Gln Phe Asn Pro Val Lys Asn Leu Lys Ala Gln Pro Asp Gly
            1380                1385                1390

Gly Asp Val Val Leu Lys Trp Glu Ala Pro Ser Ala Lys Lys Thr Glu
            1395                1400                1405

Gly Ser Arg Glu Val Lys Arg Ile Gly Asp Gly Leu Phe Val Thr Ile
        1410                1415                1420

Glu Pro Ala Asn Asp Val Arg Ala Asn Glu Ala Lys Val Val Leu Ala
1425                1430                1435                1440

Ala Asp Asn Val Trp Gly Asp Asn Thr Gly Tyr Gln Phe Leu Leu Asp
            1445                1450                1455

Ala Asp His Asn Thr Phe Gly Ser Val Ile Pro Ala Thr Gly Pro Leu
            1460                1465                1470

Phe Thr Gly Thr Ala Ser Ser Asp Leu Tyr Ser Ala Asn Phe Glu Ser
            1475                1480                1485

Leu Ile Pro Ala Asn Ala Asp Pro Val Val Thr Thr Gln Asn Ile Ile
            1490                1495                1500

Val Thr Gly Gln Gly Glu Val Val Ile Pro Gly Gly Val Tyr Asp Tyr
1505                1510                1515                1520

Cys Ile Thr Asn Pro Glu Pro Ala Ser Gly Lys Met Trp Ile Ala Gly
            1525                1530                1535

Asp Gly Gly Asn Gln Pro Ala Arg Tyr Asp Asp Phe Thr Phe Glu Ala
            1540                1545                1550

Gly Lys Lys Tyr Thr Phe Thr Met Arg Arg Ala Gly Met Gly Asp Gly
            1555                1560                1565

Thr Asp Met Glu Val Glu Asp Asp Ser Pro Ala Ser Tyr Thr Tyr Thr
        1570                1575                1580

Val Tyr Arg Asp Gly Thr Lys Ile Lys Glu Gly Leu Thr Glu Thr Thr
1585                1590                1595                1600

Tyr Arg Asp Ala Gly Met Ser Ala Gln Ser His Glu Tyr Cys Val Glu
            1605                1610                1615

Val Lys Tyr Thr Ala Gly Val Ser Pro Lys Val Cys Val Asp Tyr Ile
            1620                1625                1630

Pro Asp Gly Val Ala Asp Val Thr Ala Gln Lys Pro Tyr Thr Leu Thr
            1635                1640                1645

Val Val Gly Lys Thr Ile Thr Val Thr Cys Gln Gly Glu Ala Met Ile
            1650                1655                1660

Tyr Asp Met Asn Gly Arg Arg Leu Ala Ala Gly Arg Asn Thr Val Val
1665                1670                1675                1680

Tyr Thr Ala Gln Gly Gly Tyr Tyr Ala Val Met Val Val Val Asp Gly
            1685                1690                1695

Lys Ser Tyr Val Glu Lys Leu Ala Ile Lys
```

```
                        1700                1705

<210> SEQ ID NO 2
<211> LENGTH: 1732
<212> TYPE: PRT
<213> ORGANISM: Porphyromonas gingivalis

<400> SEQUENCE: 2

Met Arg Lys Leu Leu Leu Ile Ala Ala Ser Leu Leu Gly Val Gly
  1               5                  10                  15

Leu Tyr Ala Gln Ser Ala Lys Ile Lys Leu Asp Ala Pro Thr Thr Arg
             20                  25                  30

Thr Thr Cys Thr Asn Asn Ser Phe Lys Gln Phe Asp Ala Ser Phe Ser
         35                  40                  45

Phe Asn Glu Val Glu Leu Thr Lys Val Glu Thr Lys Gly Gly Thr Phe
 50                  55                  60

Ala Ser Val Ser Ile Pro Gly Ala Phe Pro Thr Gly Glu Val Gly Ser
 65                  70                  75                  80

Pro Glu Val Pro Ala Val Arg Lys Leu Ile Ala Val Pro Val Gly Ala
             85                  90                  95

Thr Pro Val Val Arg Val Lys Ser Phe Thr Glu Gln Val Tyr Ser Leu
            100                 105                 110

Asn Gln Tyr Gly Ser Glu Lys Leu Met Pro His Gln Pro Ser Met Ser
            115                 120                 125

Lys Ser Asp Asp Pro Glu Lys Val Pro Phe Val Tyr Asn Ala Ala Ala
130                 135                 140

Tyr Ala Arg Lys Gly Phe Val Gly Gln Glu Leu Thr Gln Val Glu Met
145                 150                 155                 160

Leu Gly Thr Met Arg Gly Val Arg Ile Ala Ala Leu Thr Ile Asn Pro
                165                 170                 175

Val Gln Tyr Asp Val Val Ala Asn Gln Leu Lys Val Arg Asn Asn Ile
            180                 185                 190

Glu Ile Glu Val Ser Phe Gln Gly Ala Asp Glu Val Ala Thr Gln Arg
        195                 200                 205

Leu Tyr Asp Ala Ser Phe Ser Pro Tyr Phe Glu Thr Ala Tyr Lys Gln
210                 215                 220

Leu Phe Asn Arg Asp Val Tyr Thr Asp His Gly Asp Leu Tyr Asn Thr
225                 230                 235                 240

Pro Val Arg Met Leu Val Ala Gly Ala Lys Phe Lys Glu Ala Leu
            245                 250                 255

Lys Pro Trp Leu Thr Trp Lys Ala Gln Lys Gly Phe Tyr Leu Asp Val
                260                 265                 270

His Tyr Thr Asp Glu Ala Glu Val Gly Thr Thr Asn Ala Ser Ile Lys
            275                 280                 285

Ala Phe Ile His Lys Lys Tyr Asn Asp Gly Leu Ala Ala Ser Ala Ala
290                 295                 300

Pro Val Phe Leu Ala Leu Val Gly Asp Thr Asp Val Ile Ser Gly Glu
305                 310                 315                 320

Lys Gly Lys Lys Thr Lys Lys Val Thr Asp Leu Tyr Tyr Ser Ala Val
                325                 330                 335

Asp Gly Asp Tyr Phe Pro Glu Met Tyr Thr Phe Arg Met Ser Ala Ser
            340                 345                 350

Ser Pro Glu Glu Leu Thr Asn Ile Ile Asp Lys Val Leu Met Tyr Glu
        355                 360                 365
```

-continued

```
Lys Ala Thr Met Pro Asp Lys Ser Tyr Leu Glu Lys Val Leu Leu Ile
    370                 375                 380
Ala Gly Ala Asp Tyr Ser Trp Asn Ser Gln Val Gly Gln Pro Thr Ile
385                 390                 395                 400
Lys Tyr Gly Met Gln Tyr Tyr Asn Gln Glu His Gly Tyr Thr Asp
                405                 410                 415
Val Tyr Asn Tyr Leu Lys Ala Pro Tyr Thr Gly Cys Tyr Ser His Leu
        420                 425                 430
Asn Thr Gly Val Ser Phe Ala Asn Tyr Thr Ala His Gly Ser Glu Thr
            435                 440                 445
Ala Trp Ala Asp Pro Leu Leu Thr Thr Ser Gln Leu Lys Ala Leu Thr
450                 455                 460
Asn Lys Asp Lys Tyr Phe Leu Ala Ile Gly Asn Cys Cys Ile Thr Ala
465                 470                 475                 480
Gln Phe Asp Tyr Val Gln Pro Cys Phe Gly Glu Val Ile Thr Arg Val
                485                 490                 495
Lys Glu Lys Gly Ala Tyr Ala Tyr Ile Gly Ser Ser Pro Asn Ser Tyr
                500                 505                 510
Trp Gly Glu Asp Tyr Tyr Trp Ser Val Gly Ala Asn Ala Val Phe Gly
            515                 520                 525
Val Gln Pro Thr Phe Glu Gly Thr Ser Met Gly Ser Tyr Asp Ala Thr
        530                 535                 540
Phe Leu Glu Asp Ser Tyr Asn Thr Val Asn Ser Ile Met Trp Ala Gly
545                 550                 555                 560
Asn Leu Ala Ala Thr His Ala Gly Asn Ile Gly Asn Ile Thr His Ile
                565                 570                 575
Gly Ala His Tyr Tyr Trp Glu Ala Tyr His Val Leu Gly Asp Gly Ser
            580                 585                 590
Val Met Pro Tyr Arg Ala Met Pro Lys Thr Asn Thr Tyr Thr Leu Pro
        595                 600                 605
Ala Ser Leu Pro Gln Asn Gln Ala Ser Tyr Ser Ile Gln Ala Ser Ala
        610                 615                 620
Gly Ser Tyr Val Ala Ile Ser Lys Asp Gly Val Leu Tyr Gly Thr Gly
625                 630                 635                 640
Val Ala Asn Ala Ser Gly Val Ala Thr Val Ser Met Thr Lys Gln Ile
                645                 650                 655
Thr Glu Asn Gly Asn Tyr Asp Val Val Ile Thr Arg Ser Asn Tyr Leu
                660                 665                 670
Pro Val Ile Lys Gln Ile Gln Val Gly Glu Pro Ser Pro Tyr Gln Pro
            675                 680                 685
Val Ser Asn Leu Thr Ala Thr Thr Gln Gly Gln Lys Val Thr Leu Lys
        690                 695                 700
Trp Glu Ala Pro Ser Ala Lys Lys Ala Glu Gly Ser Arg Glu Val Lys
705                 710                 715                 720
Arg Ile Gly Asp Gly Leu Phe Val Thr Ile Glu Pro Ala Asn Asp Val
                725                 730                 735
Arg Ala Asn Glu Ala Lys Val Val Leu Ala Ala Asp Asn Val Trp Gly
            740                 745                 750
Asp Asn Thr Gly Tyr Gln Phe Leu Asp Ala Asp His Asn Thr Phe
        755                 760                 765
Gly Ser Val Ile Pro Ala Thr Gly Pro Leu Phe Thr Gly Thr Ala Ser
    770                 775                 780
Ser Asn Leu Tyr Ser Ala Asn Phe Glu Tyr Leu Ile Pro Ala Asn Ala
```

```
            785                 790                 795                 800
Asp Pro Val Val Thr Thr Gln Asn Ile Ile Val Thr Gly Gln Gly Glu
                805                 810                 815

Val Val Ile Pro Gly Gly Val Tyr Asp Tyr Cys Ile Thr Asn Pro Glu
                820                 825                 830

Pro Ala Ser Gly Lys Met Trp Ile Ala Gly Asp Gly Asn Gln Pro
                835                 840                 845

Ala Arg Tyr Asp Asp Phe Thr Phe Glu Ala Gly Lys Lys Tyr Thr Phe
                850                 855                 860

Thr Met Arg Arg Ala Gly Met Gly Asp Gly Thr Asp Met Glu Val Glu
865                 870                 875                 880

Asp Asp Ser Pro Ala Ser Tyr Thr Tyr Thr Val Tyr Arg Asp Gly Thr
                885                 890                 895

Lys Ile Lys Glu Gly Leu Thr Ala Thr Thr Phe Glu Glu Asp Gly Val
                900                 905                 910

Ala Ala Gly Asn His Glu Tyr Cys Val Glu Val Lys Tyr Thr Ala Gly
                915                 920                 925

Val Ser Pro Lys Val Cys Lys Asp Val Thr Val Glu Gly Ser Asn Glu
                930                 935                 940

Phe Ala Pro Val Gln Asn Leu Thr Gly Ser Ser Val Gly Gln Lys Val
945                 950                 955                 960

Thr Leu Lys Trp Asp Ala Pro Asn Gly Thr Pro Asn Pro Asn Pro Asn
                965                 970                 975

Pro Asn Pro Asn Pro Gly Thr Thr Leu Ser Glu Ser Phe Glu Asn Gly
                980                 985                 990

Ile Pro Ala Ser Trp Lys Thr Ile Asp Ala Asp Gly Asp Gly His Gly
                995                 1000                1005

Trp Lys Pro Gly Asn Ala Pro Gly Ile Ala Gly Tyr Asn Ser Asn Gly
                1010                1015                1020

Cys Val Tyr Ser Glu Ser Phe Gly Leu Gly Gly Ile Gly Val Leu Thr
1025                1030                1035                1040

Pro Asp Asn Tyr Leu Ile Thr Pro Ala Leu Asp Leu Pro Asn Gly Gly
                1045                1050                1055

Lys Leu Thr Phe Trp Val Cys Ala Gln Asp Ala Asn Tyr Ala Ser Glu
                1060                1065                1070

His Tyr Ala Val Tyr Ala Ser Ser Thr Gly Asn Asp Ala Ser Asn Phe
                1075                1080                1085

Thr Asn Ala Leu Leu Glu Glu Thr Ile Thr Ala Lys Gly Val Arg Ser
                1090                1095                1100

Pro Lys Ala Ile Arg Gly Arg Ile Gln Gly Thr Trp Arg Gln Lys Thr
1105                1110                1115                1120

Val Asp Leu Pro Ala Gly Thr Lys Tyr Val Ala Phe Arg His Phe Gln
                1125                1130                1135

Ser Thr Asp Met Phe Tyr Ile Asp Leu Asp Glu Val Glu Ile Lys Ala
                1140                1145                1150

Asn Gly Lys Arg Ala Asp Phe Thr Glu Thr Phe Glu Ser Ser Thr His
                1155                1160                1165

Gly Glu Ala Pro Ala Glu Trp Thr Thr Ile Asp Ala Asp Gly Asp Gly
                1170                1175                1180

Gln Gly Trp Leu Cys Leu Ser Ser Gly Gln Leu Asp Trp Leu Thr Ala
1185                1190                1195                1200

His Gly Gly Ser Asn Val Val Ser Ser Phe Ser Trp Asn Gly Met Ala
                1205                1210                1215
```

```
Leu Asn Pro Asp Asn Tyr Leu Ile Ser Lys Asp Val Thr Gly Ala Thr
            1220                1225                1230

Lys Val Lys Tyr Tyr Ala Val Asn Asp Gly Phe Pro Gly Asp His
        1235                1240                1245

Tyr Ala Val Met Ile Ser Lys Thr Gly Thr Asn Ala Gly Asp Phe Thr
    1250                1255                1260

Val Val Phe Glu Glu Thr Pro Asn Gly Ile Asn Lys Gly Gly Ala Arg
1265                1270                1275                1280

Phe Gly Leu Ser Thr Glu Ala Asn Gly Ala Lys Pro Gln Ser Val Trp
            1285                1290                1295

Ile Glu Arg Thr Val Asp Leu Pro Ala Gly Thr Lys Tyr Val Ala Phe
        1300                1305                1310

Arg His Tyr Asn Cys Ser Asp Leu Asn Tyr Ile Leu Leu Asp Asp Ile
        1315                1320                1325

Gln Phe Thr Met Gly Gly Ser Pro Thr Pro Thr Asp Tyr Thr Tyr Thr
        1330                1335                1340

Val Tyr Arg Asp Gly Thr Lys Ile Lys Glu Gly Leu Thr Glu Thr Thr
1345                1350                1355                1360

Phe Glu Glu Asp Gly Val Ala Thr Gly Asn His Glu Tyr Cys Val Glu
            1365                1370                1375

Val Lys Tyr Thr Ala Gly Val Ser Pro Lys Lys Cys Val Asn Val Thr
            1380                1385                1390

Val Asn Ser Thr Gln Phe Asn Pro Val Gln Asn Leu Thr Ala Glu Gln
        1395                1400                1405

Ala Pro Asn Ser Met Asp Ala Ile Leu Lys Trp Asn Ala Pro Ala Ser
        1410                1415                1420

Lys Arg Ala Glu Val Leu Asn Glu Asp Phe Glu Asn Gly Ile Pro Ala
1425                1430                1435                1440

Ser Trp Lys Thr Ile Asp Ala Asp Gly Asp Gly Asn Asn Trp Thr Thr
            1445                1450                1455

Thr Pro Pro Pro Gly Gly Ser Ser Phe Ala Gly His Asn Ser Ala Ile
            1460                1465                1470

Cys Val Ser Ser Ala Ser Tyr Ile Asn Phe Glu Gly Pro Gln Asn Pro
        1475                1480                1485

Asp Asn Tyr Leu Val Thr Pro Glu Leu Ser Leu Pro Gly Gly Gly Thr
        1490                1495                1500

Leu Thr Phe Trp Val Cys Ala Gln Asp Ala Asn Tyr Ala Ser Glu His
1505                1510                1515                1520

Tyr Ala Val Tyr Ala Ser Ser Thr Gly Asn Asp Ala Ser Asn Phe Ala
            1525                1530                1535

Asn Ala Leu Leu Glu Glu Val Leu Thr Ala Lys Thr Val Thr Ala
            1540                1545                1550

Pro Glu Ala Ile Arg Gly Thr Arg Ala Gln Gly Thr Trp Tyr Gln Lys
        1555                1560                1565

Thr Val Gln Leu Pro Ala Gly Thr Lys Tyr Val Ala Phe Arg His Phe
        1570                1575                1580

Gly Cys Thr Asp Phe Phe Trp Ile Asn Leu Asp Asp Val Val Ile Thr
1585                1590                1595                1600

Ser Gly Asn Ala Pro Ser Tyr Thr Tyr Thr Ile Tyr Arg Asn Asn Thr
            1605                1610                1615

Gln Ile Ala Ser Gly Val Thr Glu Thr Thr Tyr Arg Asp Pro Asp Leu
        1620                1625                1630
```

```
Ala Thr Gly Phe Tyr Thr Tyr Gly Val Lys Val Val Tyr Pro Asn Gly
    1635                1640                1645

Glu Ser Ala Ile Glu Thr Ala Thr Leu Asn Ile Thr Ser Leu Ala Asp
    1650                1655                1660

Val Thr Ala Gln Lys Pro Tyr Thr Leu Thr Val Val Gly Lys Thr Ile
1665                1670                1675                1680

Thr Val Thr Cys Gln Gly Glu Ala Met Ile Tyr Asp Met Asn Gly Arg
            1685                1690                1695

Arg Leu Ala Ala Gly Arg Asn Thr Val Val Tyr Thr Ala Gln Gly Gly
                1700                1705                1710

His Tyr Ala Val Met Val Val Asp Gly Lys Ser Tyr Val Glu Lys
            1715                1720                1725

Leu Ala Val Lys
    1730

<210> SEQ ID NO 3
<211> LENGTH: 2164
<212> TYPE: PRT
<213> ORGANISM: Porphyromonas gingivalis

<400> SEQUENCE: 3

Met Arg Lys Leu Asn Ser Leu Phe Ser Leu Ala Val Leu Leu Ser Leu
1               5                   10                  15

Leu Cys Trp Gly Gln Thr Ala Ala Ala Gln Gly Gly Pro Lys Thr Ala
                20                  25                  30

Pro Ser Val Thr His Gln Ala Val Gln Lys Gly Ile Arg Thr Ser Lys
            35                  40                  45

Ala Lys Asp Leu Arg Asp Pro Ile Pro Ala Gly Met Ala Arg Ile Ile
50                  55                  60

Leu Glu Ala His Asp Val Trp Glu Asp Gly Thr Gly Tyr Gln Met Leu
65                  70                  75                  80

Trp Asp Ala Asp His Asn Gln Tyr Gly Ala Ser Ile Pro Glu Glu Ser
                85                  90                  95

Phe Trp Phe Ala Asn Gly Thr Ile Pro Ala Gly Leu Tyr Asp Pro Phe
            100                 105                 110

Glu Tyr Lys Val Pro Val Asn Ala Asp Ala Ser Phe Ser Pro Thr Asn
            115                 120                 125

Phe Val Leu Asp Gly Thr Ala Ser Ala Asp Ile Pro Ala Gly Thr Tyr
    130                 135                 140

Asp Tyr Val Ile Ile Asn Pro Asn Pro Gly Ile Ile Tyr Ile Val Gly
145                 150                 155                 160

Glu Gly Val Ser Lys Gly Asn Asp Tyr Val Val Glu Ala Gly Lys Thr
                165                 170                 175

Tyr His Phe Thr Val Gln Arg Gln Gly Pro Gly Asp Ala Ala Ser Val
            180                 185                 190

Val Val Thr Gly Glu Gly Gly Asn Glu Phe Ala Pro Val Gln Asn Leu
    195                 200                 205

Gln Trp Ser Val Ser Gly Gln Thr Val Thr Leu Thr Trp Gln Ala Pro
    210                 215                 220

Ala Ser Asp Lys Arg Thr Tyr Val Leu Asn Glu Ser Phe Asp Thr Gln
225                 230                 235                 240

Thr Leu Pro Asn Gly Trp Thr Met Ile Asp Ala Asp Gly Asp Gly His
            245                 250                 255

Asn Trp Leu Ser Thr Ile Asn Val Tyr Asn Thr Ala Thr His Thr Gly
            260                 265                 270
```

-continued

```
Asp Gly Ala Met Phe Ser Lys Ser Trp Thr Ala Ser Ser Gly Ala Lys
            275                 280                 285

Ile Asp Leu Ser Pro Asp Asn Tyr Leu Val Thr Pro Lys Phe Thr Val
290                 295                 300

Pro Glu Asn Gly Lys Leu Ser Tyr Trp Val Ser Ser Gln Pro Trp
305                 310                 315                 320

Thr Asn Glu His Tyr Gly Val Phe Leu Ser Thr Gly Asn Glu Ala
                325                 330                 335

Ala Asn Phe Thr Ile Lys Leu Leu Glu Glu Thr Leu Gly Ser Gly Lys
            340                 345                 350

Pro Ala Pro Met Asn Leu Val Lys Ser Glu Gly Val Lys Ala Pro Ala
            355                 360                 365

Pro Tyr Gln Glu Arg Thr Ile Asp Leu Ser Ala Tyr Ala Gly Gln Gln
370                 375                 380

Val Tyr Leu Ala Phe Arg His Phe Gly Cys Thr Gly Ile Phe Arg Leu
385                 390                 395                 400

Tyr Leu Asp Asp Val Ala Val Ser Gly Glu Gly Ser Ser Asn Asp Tyr
                405                 410                 415

Thr Tyr Thr Val Tyr Arg Asp Asn Val Val Ile Ala Gln Asn Leu Thr
                420                 425                 430

Ala Thr Thr Phe Asn Gln Glu Asn Val Ala Pro Gly Gln Tyr Asn Tyr
            435                 440                 445

Cys Val Glu Val Lys Tyr Thr Ala Gly Val Ser Pro Lys Val Cys Lys
450                 455                 460

Asp Val Thr Val Glu Gly Ser Asn Glu Phe Ala Pro Val Gln Asn Leu
465                 470                 475                 480

Thr Gly Ser Ala Val Gly Gln Lys Val Thr Leu Lys Trp Asp Ala Pro
                485                 490                 495

Asn Gly Thr Pro Asn Pro Asn Pro Gly Thr Thr Thr Leu Ser Glu Ser
            500                 505                 510

Phe Glu Asn Gly Ile Pro Ala Ser Trp Lys Thr Ile Asp Ala Asp Gly
            515                 520                 525

Asp Gly Asn Asn Trp Thr Thr Thr Pro Pro Gly Gly Ser Ser Phe
530                 535                 540

Ala Gly His Asn Ser Ala Ile Cys Val Ser Ser Ala Ser Tyr Ile Asn
545                 550                 555                 560

Phe Glu Gly Pro Gln Asn Pro Asp Asn Tyr Leu Val Thr Pro Glu Leu
                565                 570                 575

Ser Leu Pro Asn Gly Gly Thr Leu Thr Phe Trp Val Cys Ala Gln Asp
            580                 585                 590

Ala Asn Tyr Ala Ser Glu His Tyr Ala Val Tyr Ala Ser Ser Thr Gly
            595                 600                 605

Asn Asp Ala Ser Asn Phe Ala Asn Ala Leu Leu Glu Glu Val Leu Thr
610                 615                 620

Ala Lys Thr Val Val Thr Ala Pro Glu Ala Ile Arg Gly Thr Arg Val
625                 630                 635                 640

Gln Gly Thr Trp Tyr Gln Lys Thr Val Gln Leu Pro Ala Gly Thr Lys
                645                 650                 655

Tyr Val Ala Phe Arg His Phe Gly Cys Thr Asp Phe Phe Trp Ile Asn
                660                 665                 670

Leu Asp Asp Val Glu Ile Lys Ala Asn Gly Lys Arg Ala Asp Phe Thr
            675                 680                 685
```

-continued

```
Glu Thr Phe Glu Ser Ser Thr His Gly Glu Ala Pro Ala Glu Trp Thr
    690             695                 700

Thr Ile Asp Ala Asp Gly Asp Gly Gln Gly Trp Leu Cys Leu Ser Ser
705             710              715                 720

Gly Gln Leu Gly Trp Leu Thr Ala His Gly Thr Asn Val Val Ala
            725             730                 735

Ser Phe Ser Trp Asn Gly Met Ala Leu Asn Pro Asp Asn Tyr Leu Ile
        740             745             750

Ser Lys Asp Val Thr Gly Ala Thr Lys Val Lys Tyr Tyr Tyr Ala Val
        755             760             765

Asn Asp Gly Phe Pro Gly Asp His Tyr Ala Val Met Ile Ser Lys Thr
770             775             780

Gly Thr Asn Ala Gly Asp Phe Thr Val Val Phe Glu Glu Thr Pro Asn
785             790             795                 800

Gly Ile Asn Lys Gly Ala Arg Phe Gly Leu Ser Thr Glu Ala Asn
            805             810             815

Gly Ala Lys Pro Gln Ser Val Trp Ile Glu Arg Thr Val Asp Leu Pro
        820             825             830

Ala Gly Thr Lys Tyr Val Ala Phe Arg His Tyr Asn Cys Ser Asp Leu
        835             840             845

Asn Tyr Ile Leu Leu Asp Asp Ile Gln Phe Thr Met Gly Gly Ser Pro
850             855             860

Thr Pro Thr Asp Tyr Thr Tyr Thr Val Tyr Arg Asp Gly Thr Lys Ile
865             870             875             880

Lys Glu Gly Leu Thr Glu Thr Thr Phe Glu Glu Asp Gly Val Ala Thr
            885             890             895

Gly Asn His Glu Tyr Cys Val Glu Val Lys Tyr Thr Ala Gly Val Ser
        900             905             910

Pro Lys Glu Cys Val Asn Val Thr Val Asp Pro Val Gln Phe Asn Pro
        915             920             925

Val Gln Asn Leu Thr Gly Ser Ala Val Gly Gln Lys Val Thr Leu Lys
    930             935             940

Trp Asp Ala Pro Asn Gly Thr Pro Asn Pro Asn Pro Gly Thr Thr Thr
945             950             955                 960

Leu Ser Glu Ser Phe Glu Asn Gly Ile Pro Ala Ser Trp Lys Thr Ile
            965             970             975

Asp Ala Asp Gly Asp Gly Asn Asn Trp Thr Thr Pro Pro Gly
            980             985             990

Gly Thr Ser Phe Ala Gly His Asn Ser Ala Ile Cys Val Ser Ser Ala
        995             1000            1005

Ser Tyr Ile Asn Phe Glu Gly Pro Gln Asn Pro Asp Asn Tyr Leu Val
    1010            1015            1020

Thr Pro Glu Leu Ser Leu Pro Asn Gly Gly Thr Leu Thr Phe Trp Val
1025            1030            1035                1040

Cys Ala Gln Asp Ala Asn Tyr Ala Ser Glu His Tyr Ala Val Tyr Ala
                1045            1050            1055

Ser Ser Thr Gly Asn Asp Ala Ser Asn Phe Ala Asn Ala Leu Leu Glu
            1060            1065            1070

Glu Val Leu Thr Ala Lys Thr Val Thr Ala Pro Glu Ala Ile Arg
        1075            1080            1085

Gly Thr Arg Val Gln Gly Thr Trp Tyr Gln Lys Thr Val Gln Leu Pro
    1090            1095            1100

Ala Gly Thr Lys Tyr Val Ala Phe Arg His Phe Gly Cys Thr Asp Phe
```

```
                    1105                1110                1115                1120
            Phe Trp Ile Asn Leu Asp Asp Val Glu Ile Lys Ala Asn Gly Lys Arg
                        1125                1130                1135
            Ala Asp Phe Thr Glu Thr Phe Glu Ser Ser Thr His Gly Glu Ala Pro
                    1140                1145                1150
            Ala Glu Trp Thr Thr Ile Asp Ala Asp Gly Asp Gly Gln Gly Trp Leu
                1155                1160                1165
            Cys Leu Ser Ser Gly Gln Leu Asp Trp Leu Thr Ala His Gly Gly Thr
                1170                1175                1180
            Asn Val Val Ala Ser Phe Ser Trp Asn Gly Met Ala Leu Asn Pro Asp
        1185                1190                1195                1200
            Asn Tyr Leu Ile Ser Lys Asp Val Thr Gly Ala Thr Lys Val Lys Tyr
                        1205                1210                1215
            Tyr Tyr Ala Val Asn Asp Gly Phe Pro Gly Asp His Tyr Ala Val Met
                    1220                1225                1230
            Ile Ser Lys Thr Gly Thr Asn Ala Gly Asp Phe Thr Val Val Phe Glu
                        1235                1240                1245
            Glu Thr Pro Asn Gly Ile Asn Lys Gly Gly Ala Arg Phe Gly Leu Ser
                    1250                1255                1260
            Thr Glu Ala Asn Gly Ala Lys Pro Gln Ser Val Trp Ile Glu Arg Thr
        1265                1270                1275                1280
            Val Asp Leu Pro Ala Gly Thr Lys Tyr Val Ala Phe Arg His Tyr Asn
                        1285                1290                1295
            Cys Ser Asp Leu Asn Tyr Ile Leu Leu Asp Asp Ile Gln Phe Thr Met
                    1300                1305                1310
            Gly Gly Ser Pro Thr Pro Thr Asp Tyr Thr Tyr Thr Val Tyr Arg Asp
                    1315                1320                1325
            Gly Thr Lys Ile Lys Glu Gly Leu Thr Glu Thr Phe Glu Glu Asp
                        1330                1335                1340
            Gly Val Ala Thr Gly Asn His Glu Tyr Cys Val Glu Val Lys Tyr Thr
        1345                1350                1355                1360
            Ala Gly Val Ser Pro Lys Glu Cys Val Asn Val Thr Val Asp Pro Val
                        1365                1370                1375
            Gln Phe Asn Pro Val Gln Asn Leu Thr Gly Ser Ala Val Gly Gln Lys
                        1380                1385                1390
            Val Thr Leu Lys Trp Asp Ala Pro Asn Gly Thr Pro Asn Pro Asn Pro
                    1395                1400                1405
            Gly Thr Thr Thr Leu Ser Glu Ser Phe Glu Asn Gly Ile Pro Ala Ser
                    1410                1415                1420
            Trp Lys Thr Ile Asp Ala Asp Gly Asp Gly Asn Asn Trp Thr Thr Thr
        1425                1430                1435                1440
            Pro Pro Pro Gly Gly Thr Ser Phe Ala Gly His Asn Ser Ala Ile Cys
                        1445                1450                1455
            Val Ser Ser Ala Ser Tyr Ile Asn Phe Glu Gly Pro Gln Asn Pro Asp
                        1460                1465                1470
            Asn Tyr Leu Val Thr Pro Glu Leu Ser Leu Pro Asn Gly Gly Thr Leu
                    1475                1480                1485
            Thr Phe Trp Val Cys Ala Gln Asp Ala Asn Tyr Ala Ser Glu His Tyr
                    1490                1495                1500
            Ala Val Tyr Ala Ser Ser Thr Gly Asn Asp Ala Ser Asn Phe Ala Asn
        1505                1510                1515                1520
            Ala Leu Leu Glu Glu Val Leu Thr Ala Lys Thr Val Val Thr Ala Pro
                        1525                1530                1535
```

```
Glu Ala Ile Arg Gly Thr Arg Val Gln Gly Thr Trp Tyr Gln Lys Thr
        1540                1545                1550

Val Gln Leu Pro Ala Gly Thr Lys Tyr Val Ala Phe Arg His Phe Gly
        1555                1560                1565

Cys Thr Asp Phe Phe Trp Ile Asn Leu Asp Asp Val Glu Ile Lys Ala
        1570                1575                1580

Asn Gly Lys Arg Ala Asp Phe Thr Glu Thr Phe Glu Ser Ser Thr His
1585                1590                1595                1600

Gly Glu Ala Pro Ala Glu Trp Thr Thr Ile Asp Ala Asp Gly Asp Gly
            1605                1610                1615

Gln Gly Trp Leu Cys Leu Ser Ser Gly Gln Leu Gly Trp Leu Thr Ala
        1620                1625                1630

His Gly Gly Thr Asn Val Val Ala Ser Phe Ser Trp Asn Gly Met Ala
        1635                1640                1645

Leu Asn Pro Asp Asn Tyr Leu Ile Ser Lys Asp Val Thr Gly Ala Thr
        1650                1655                1660

Lys Val Lys Tyr Tyr Ala Val Asn Asp Gly Phe Pro Gly Asp His
1665                1670                1675                1680

Tyr Ala Val Met Ile Ser Lys Thr Gly Thr Asn Ala Gly Asp Phe Thr
            1685                1690                1695

Val Val Phe Glu Glu Thr Pro Asn Gly Ile Asn Lys Gly Gly Ala Arg
        1700                1705                1710

Phe Gly Leu Ser Thr Glu Ala Asn Gly Ala Lys Pro Gln Ser Val Trp
        1715                1720                1725

Ile Glu Arg Thr Val Asp Leu Pro Ala Gly Thr Lys Tyr Val Ala Phe
        1730                1735                1740

Arg His Tyr Asn Cys Ser Asp Leu Asn Tyr Ile Leu Leu Asp Asp Ile
1745                1750                1755                1760

Gln Phe Thr Met Gly Gly Ser Pro Thr Pro Thr Asp Tyr Thr Tyr Thr
            1765                1770                1775

Val Tyr Arg Asp Gly Thr Lys Ile Lys Glu Gly Leu Thr Glu Thr Thr
        1780                1785                1790

Phe Glu Glu Asp Gly Val Ala Thr Gly Asn His Glu Tyr Cys Val Glu
        1795                1800                1805

Val Lys Tyr Thr Ala Gly Val Ser Pro Lys Glu Cys Val Asn Val Thr
        1810                1815                1820

Ile Asn Pro Thr Gln Phe Asn Pro Val Gln Asn Leu Thr Ala Glu Gln
1825                1830                1835                1840

Ala Pro Asn Ser Met Asp Ala Ile Leu Lys Trp Asn Ala Pro Ala Ser
            1845                1850                1855

Lys Arg Ala Glu Val Leu Asn Glu Asp Phe Glu Asn Gly Ile Pro Ala
        1860                1865                1870

Ser Trp Lys Thr Ile Asp Ala Asp Gly Asp Gly Asn Asn Trp Thr Thr
        1875                1880                1885

Thr Pro Pro Gly Gly Ser Ser Phe Ala Gly His Asn Ser Ala Ile
        1890                1895                1900

Cys Val Ser Ser Ala Ser Tyr Ile Asn Phe Glu Gly Pro Gln Asn Pro
1905                1910                1915                1920

Asp Asn Tyr Leu Val Thr Pro Glu Leu Ser Leu Pro Gly Gly Gly Thr
            1925                1930                1935

Leu Thr Phe Trp Val Cys Ala Gln Asp Ala Asn Tyr Ala Ser Glu His
        1940                1945                1950
```

```
Tyr Ala Val Tyr Ala Ser Ser Thr Gly Asn Asp Ala Ser Asn Phe Ala
        1955                1960                1965

Asn Ala Leu Leu Glu Glu Val Leu Thr Ala Lys Thr Val Val Thr Ala
    1970                1975                1980

Pro Glu Ala Ile Arg Gly Thr Arg Val Gln Gly Thr Trp Tyr Gln Lys
1985                1990                1995                2000

Thr Val Gln Leu Pro Ala Gly Thr Lys Tyr Val Ala Phe Arg His Phe
            2005                2010                2015

Gly Cys Thr Asp Phe Phe Trp Ile Asn Leu Asp Asp Val Val Ile Thr
        2020                2025                2030

Ser Gly Asn Ala Pro Ser Tyr Thr Tyr Thr Ile Tyr Arg Asn Asn Thr
    2035                2040                2045

Gln Ile Ala Ser Gly Val Thr Glu Thr Thr Tyr Arg Asp Pro Asp Leu
2050                2055                2060

Ala Thr Gly Phe Tyr Thr Tyr Gly Val Lys Val Val Tyr Pro Asn Gly
2065                2070                2075                2080

Glu Ser Ala Ile Glu Thr Ala Thr Leu Asn Ile Thr Ser Leu Ala Asp
            2085                2090                2095

Val Thr Ala Gln Lys Pro Tyr Thr Leu Thr Val Gly Lys Thr Ile
        2100                2105                2110

Thr Val Thr Cys Gln Gly Glu Ala Met Ile Tyr Asp Met Asn Gly Arg
        2115                2120                2125

Arg Leu Ala Ala Gly Arg Asn Thr Val Val Tyr Thr Ala Gln Gly Gly
        2130                2135                2140

His Tyr Ala Val Met Val Val Val Asp Gly Lys Ser Tyr Val Glu Lys
2145                2150                2155                2160

Leu Ala Val Lys

<210> SEQ ID NO 4
<211> LENGTH: 15
<212> TYPE: PRT
<213> ORGANISM: Porphyromonas gingivalis

<400> SEQUENCE: 4

Gln Phe Asp Ala Ser Phe Ser Phe Asn Glu Val Glu Leu Thr Lys
1               5                   10                  15

<210> SEQ ID NO 5
<211> LENGTH: 28
<212> TYPE: PRT
<213> ORGANISM: Porphyromonas gingivalis

<400> SEQUENCE: 5

Gly Gly Thr Phe Ala Ser Val Ser Ile Pro Gly Ala Phe Pro Thr Gly
1               5                   10                  15

Glu Val Gly Ser Pro Glu Val Pro Ala Val Arg Lys
            20                  25

<210> SEQ ID NO 6
<211> LENGTH: 14
<212> TYPE: PRT
<213> ORGANISM: Porphyromonas gingivalis

<400> SEQUENCE: 6

Lys Leu Ile Ala Val Pro Val Gly Ala Thr Pro Val Val Arg
1               5                   10

<210> SEQ ID NO 7
```

```
<211> LENGTH: 13
<212> TYPE: PRT
<213> ORGANISM: Porphyromonas gingivalis

<400> SEQUENCE: 7

Leu Ile Ala Val Pro Val Gly Ala Thr Pro Val Val Arg
1               5                   10

<210> SEQ ID NO 8
<211> LENGTH: 16
<212> TYPE: PRT
<213> ORGANISM: Porphyromonas gingivalis

<400> SEQUENCE: 8

Ser Phe Thr Glu Gln Val Tyr Ser Leu Asn Gln Tyr Gly Ser Glu Lys
1               5                   10                  15

<210> SEQ ID NO 9
<211> LENGTH: 18
<212> TYPE: PRT
<213> ORGANISM: Porphyromonas gingivalis

<400> SEQUENCE: 9

Ser Asp Asp Pro Glu Lys Val Pro Phe Val Tyr Asn Ala Ala Ala Tyr
1               5                   10                  15

Ala Arg

<210> SEQ ID NO 10
<211> LENGTH: 18
<212> TYPE: PRT
<213> ORGANISM: Porphyromonas gingivalis

<400> SEQUENCE: 10

Lys Gly Phe Val Gly Gln Glu Leu Thr Gln Val Glu Met Leu Gly Thr
1               5                   10                  15

Met Arg

<210> SEQ ID NO 11
<211> LENGTH: 19
<212> TYPE: PRT
<213> ORGANISM: Porphyromonas gingivalis

<400> SEQUENCE: 11

Ile Ala Ala Leu Thr Ile Asn Pro Val Gln Tyr Asp Val Val Ala Asn
1               5                   10                  15

Gln Leu Lys

<210> SEQ ID NO 12
<211> LENGTH: 19
<212> TYPE: PRT
<213> ORGANISM: Porphyromonas gingivalis

<400> SEQUENCE: 12

Asn Asn Ile Glu Ile Glu Val Ser Phe Gln Gly Ala Asp Glu Val Ala
1               5                   10                  15

Thr Gln Arg

<210> SEQ ID NO 13
<211> LENGTH: 15
<212> TYPE: PRT
<213> ORGANISM: Porphyromonas gingivalis

<400> SEQUENCE: 13
```

```
Leu Tyr Asp Ala Ser Phe Ser Pro Tyr Phe Glu Thr Ala Tyr Lys
1               5                   10                  15

<210> SEQ ID NO 14
<211> LENGTH: 15
<212> TYPE: PRT
<213> ORGANISM: Porphyromonas gingivalis

<400> SEQUENCE: 14

Asp Val Tyr Thr Asp His Gly Asp Leu Tyr Asn Thr Pro Val Arg
1               5                   10                  15

<210> SEQ ID NO 15
<211> LENGTH: 10
<212> TYPE: PRT
<213> ORGANISM: Porphyromonas gingivalis

<400> SEQUENCE: 15

Glu Ala Leu Lys Pro Trp Leu Thr Trp Lys
1               5                   10

<210> SEQ ID NO 16
<211> LENGTH: 22
<212> TYPE: PRT
<213> ORGANISM: Porphyromonas gingivalis

<400> SEQUENCE: 16

Gly Phe Tyr Leu Asp Val His Tyr Thr Asp Glu Ala Glu Val Gly Thr
1               5                   10                  15

Thr Asn Ala Ser Ile Lys
            20

<210> SEQ ID NO 17
<211> LENGTH: 27
<212> TYPE: PRT
<213> ORGANISM: Porphyromonas gingivalis

<400> SEQUENCE: 17

Tyr Asn Asp Gly Leu Ala Ala Ser Ala Ala Pro Val Phe Leu Ala Leu
1               5                   10                  15

Val Gly Asp Thr Asp Val Ile Ser Gly Glu Lys
            20                  25

<210> SEQ ID NO 18
<211> LENGTH: 21
<212> TYPE: PRT
<213> ORGANISM: Porphyromonas gingivalis

<400> SEQUENCE: 18

Val Thr Asp Leu Tyr Tyr Ser Ala Val Asp Gly Asp Tyr Phe Pro Glu
1               5                   10                  15

Met Tyr Thr Phe Arg
            20

<210> SEQ ID NO 19
<211> LENGTH: 21
<212> TYPE: PRT
<213> ORGANISM: Porphyromonas gingivalis

<400> SEQUENCE: 19

Val Leu Leu Ile Ala Gly Ala Asp Tyr Ser Trp Asn Ser Gln Val Gly
1               5                   10                  15
```

```
Gln Pro Thr Ile Lys
            20

<210> SEQ ID NO 20
<211> LENGTH: 21
<212> TYPE: PRT
<213> ORGANISM: Porphyromonas gingivalis

<400> SEQUENCE: 20

Tyr Gly Met Gln Tyr Tyr Tyr Asn Gln Glu His Gly Tyr Thr Asp Val
1               5                   10                  15

Tyr Asn Tyr Leu Lys
            20

<210> SEQ ID NO 21
<211> LENGTH: 31
<212> TYPE: PRT
<213> ORGANISM: Porphyromonas gingivalis

<400> SEQUENCE: 21

Thr Asn Thr Tyr Thr Leu Pro Ala Ser Leu Pro Gln Asn Gln Ala Ser
1               5                   10                  15

Tyr Ser Ile Gln Ala Ser Ala Gly Ser Tyr Val Ala Ile Ser Lys
            20                  25                  30

<210> SEQ ID NO 22
<211> LENGTH: 22
<212> TYPE: PRT
<213> ORGANISM: Porphyromonas gingivalis

<400> SEQUENCE: 22

Asp Gly Val Leu Tyr Gly Thr Gly Val Ala Asn Ala Ser Gly Val Ala
1               5                   10                  15

Thr Val Ser Met Thr Lys
            20

<210> SEQ ID NO 23
<211> LENGTH: 14
<212> TYPE: PRT
<213> ORGANISM: Porphyromonas gingivalis

<400> SEQUENCE: 23

Gln Ile Thr Glu Asn Gly Asn Tyr Asp Val Val Ile Thr Arg
1               5                   10

<210> SEQ ID NO 24
<211> LENGTH: 24
<212> TYPE: PRT
<213> ORGANISM: Porphyromonas gingivalis

<400> SEQUENCE: 24

Gln Ile Gln Val Gly Glu Pro Ser Pro Tyr Gln Pro Val Ser Asn Leu
1               5                   10                  15

Thr Ala Thr Thr Gln Gly Gln Lys
            20

<210> SEQ ID NO 25
<211> LENGTH: 12
<212> TYPE: PRT
<213> ORGANISM: Porphyromonas gingivalis

<400> SEQUENCE: 25

Val Pro Phe Val Tyr Asn Ala Ala Ala Tyr Ala Arg
```

```
                         1               5                    10
```

\<210\> SEQ ID NO 26
\<211\> LENGTH: 17
\<212\> TYPE: PRT
\<213\> ORGANISM: Porphyromonas gingivalis

\<400\> SEQUENCE: 26

```
Gly Phe Val Gly Gln Glu Leu Thr Gln Val Glu Met Leu Gly Thr Met
1               5                   10                  15

Arg
```

\<210\> SEQ ID NO 27
\<211\> LENGTH: 15
\<212\> TYPE: PRT
\<213\> ORGANISM: Porphyromonas gingivalis

\<400\> SEQUENCE: 27

```
Met Ser Ala Ser Ser Pro Glu Glu Leu Thr Asn Ile Ile Asp Lys
1               5                   10                  15
```

\<210\> SEQ ID NO 28
\<211\> LENGTH: 7
\<212\> TYPE: PRT
\<213\> ORGANISM: Porphyromonas gingivalis

\<400\> SEQUENCE: 28

```
Tyr Thr Pro Val Glu Glu Lys
1               5
```

\<210\> SEQ ID NO 29
\<211\> LENGTH: 19
\<212\> TYPE: PRT
\<213\> ORGANISM: Porphyromonas gingivalis

\<400\> SEQUENCE: 29

```
Val Ala Glu Asp Ile Ala Ser Pro Val Thr Ala Asn Ala Ile Gln Gln
1               5                   10                  15

Phe Val Lys
```

\<210\> SEQ ID NO 30
\<211\> LENGTH: 15
\<212\> TYPE: PRT
\<213\> ORGANISM: Porphyromonas gingivalis

\<400\> SEQUENCE: 30

```
Glu Gly Asn Asp Leu Thr Tyr Val Leu Leu Ile Gly Asp His Lys
1               5                   10                  15
```

\<210\> SEQ ID NO 31
\<211\> LENGTH: 21
\<212\> TYPE: PRT
\<213\> ORGANISM: Porphyromonas gingivalis

\<400\> SEQUENCE: 31

```
Ser Asp Gln Val Tyr Gly Gln Ile Val Gly Asn Asp His Tyr Asn Glu
1               5                   10                  15

Val Phe Ile Gly Arg
            20
```

\<210\> SEQ ID NO 32
\<211\> LENGTH: 9
\<212\> TYPE: PRT

```
<213> ORGANISM: Porphyromonas gingivalis

<400> SEQUENCE: 32

Cys Tyr Asp Pro Gly Val Thr Pro Lys
1               5

<210> SEQ ID NO 33
<211> LENGTH: 35
<212> TYPE: PRT
<213> ORGANISM: Porphyromonas gingivalis

<400> SEQUENCE: 33

Asn Ile Ile Asp Ala Phe Asn Gly Gly Ile Ser Leu Ala Asn Tyr Thr
1               5                   10                  15

Gly His Gly Ser Glu Thr Ala Trp Gly Thr Ser His Phe Gly Thr Thr
            20                  25                  30

His Val Lys
        35

<210> SEQ ID NO 34
<211> LENGTH: 24
<212> TYPE: PRT
<213> ORGANISM: Porphyromonas gingivalis

<400> SEQUENCE: 34

Asp Gly Lys Pro Thr Gly Thr Val Ala Ile Ile Ala Ser Thr Ile Asn
1               5                   10                  15

Gln Ser Trp Ala Ser Pro Met Arg
            20

<210> SEQ ID NO 35
<211> LENGTH: 12
<212> TYPE: PRT
<213> ORGANISM: Porphyromonas gingivalis

<400> SEQUENCE: 35

Gly Gln Asp Glu Met Asn Glu Ile Leu Cys Glu Lys
1               5                   10

<210> SEQ ID NO 36
<211> LENGTH: 16
<212> TYPE: PRT
<213> ORGANISM: Porphyromonas gingivalis

<400> SEQUENCE: 36

Thr Phe Gly Gly Val Thr Met Asn Gly Met Phe Ala Met Val Glu Lys
1               5                   10                  15

<210> SEQ ID NO 37
<211> LENGTH: 16
<212> TYPE: PRT
<213> ORGANISM: Porphyromonas gingivalis

<400> SEQUENCE: 37

Met Leu Asp Thr Trp Thr Val Phe Gly Asp Pro Ser Leu Leu Val Arg
1               5                   10                  15

<210> SEQ ID NO 38
<211> LENGTH: 10
<212> TYPE: PRT
<213> ORGANISM: Porphyromonas gingivalis

<400> SEQUENCE: 38
```

```
Ile Trp Ile Ala Gly Gln Gly Pro Thr Lys
1               5                   10

<210> SEQ ID NO 39
<211> LENGTH: 7
<212> TYPE: PRT
<213> ORGANISM: Porphyromonas gingivalis

<400> SEQUENCE: 39

Tyr His Phe Leu Met Lys Lys
1               5

<210> SEQ ID NO 40
<211> LENGTH: 10
<212> TYPE: PRT
<213> ORGANISM: Porphyromonas gingivalis

<400> SEQUENCE: 40

Glu Asp Asp Tyr Val Phe Glu Ala Gly Lys
1               5                   10

<210> SEQ ID NO 41
<211> LENGTH: 25
<212> TYPE: PRT
<213> ORGANISM: Porphyromonas gingivalis

<400> SEQUENCE: 41

Met Gly Ser Gly Asp Gly Thr Glu Leu Thr Ile Ser Glu Gly Gly Gly
1               5                   10                  15

Ser Asp Tyr Thr Tyr Thr Val Tyr Arg
            20                  25

<210> SEQ ID NO 42
<211> LENGTH: 25
<212> TYPE: PRT
<213> ORGANISM: Porphyromonas gingivalis

<400> SEQUENCE: 42

Glu Gly Leu Thr Ala Thr Thr Phe Glu Glu Asp Gly Val Ala Ala Gly
1               5                   10                  15

Asn His Glu Tyr Cys Val Glu Val Lys
            20                  25

<210> SEQ ID NO 43
<211> LENGTH: 24
<212> TYPE: PRT
<213> ORGANISM: Porphyromonas gingivalis

<400> SEQUENCE: 43

Asp Val Thr Val Glu Gly Ser Asn Glu Phe Ala Pro Val Gln Asn Leu
1               5                   10                  15

Thr Gly Ser Ala Val Gly Gln Lys
            20

<210> SEQ ID NO 44
<211> LENGTH: 13
<212> TYPE: PRT
<213> ORGANISM: Porphyromonas gingivalis

<400> SEQUENCE: 44

Met Trp Ile Ala Gly Asp Gly Gly Asn Gln Pro Ala Arg
1               5                   10
```

```
<210> SEQ ID NO 45
<211> LENGTH: 10
<212> TYPE: PRT
<213> ORGANISM: Porphyromonas gingivalis

<400> SEQUENCE: 45

Tyr Asp Asp Phe Thr Phe Glu Ala Gly Lys
1               5                   10

<210> SEQ ID NO 46
<211> LENGTH: 11
<212> TYPE: PRT
<213> ORGANISM: Porphyromonas gingivalis

<400> SEQUENCE: 46

Tyr Asp Asp Phe Thr Phe Glu Ala Gly Lys Lys
1               5                   10

<210> SEQ ID NO 47
<211> LENGTH: 7
<212> TYPE: PRT
<213> ORGANISM: Porphyromonas gingivalis

<400> SEQUENCE: 47

Lys Tyr Thr Phe Thr Met Arg
1               5

<210> SEQ ID NO 48
<211> LENGTH: 25
<212> TYPE: PRT
<213> ORGANISM: Porphyromonas gingivalis

<400> SEQUENCE: 48

Ala Gly Met Gly Asp Gly Thr Asp Met Glu Val Glu Asp Asp Ser Pro
1               5                   10                  15

Ala Ser Tyr Thr Tyr Thr Val Tyr Arg
            20                  25

<210> SEQ ID NO 49
<211> LENGTH: 27
<212> TYPE: PRT
<213> ORGANISM: Porphyromonas gingivalis

<400> SEQUENCE: 49

Ile Lys Glu Gly Leu Thr Ala Thr Thr Phe Glu Asp Gly Val Ala
1               5                   10                  15

Ala Gly Asn His Glu Tyr Cys Val Glu Val Lys
            20                  25

<210> SEQ ID NO 50
<211> LENGTH: 10
<212> TYPE: PRT
<213> ORGANISM: Porphyromonas gingivalis

<400> SEQUENCE: 50

Gly Arg Ile Gln Gly Thr Trp Arg Gln Lys
1               5                   10

<210> SEQ ID NO 51
<211> LENGTH: 9
<212> TYPE: PRT
<213> ORGANISM: Porphyromonas gingivalis

<400> SEQUENCE: 51
```

His Phe Gly Cys Thr Gly Ile Phe Arg
1               5

<210> SEQ ID NO 52
<211> LENGTH: 17
<212> TYPE: PRT
<213> ORGANISM: Porphyromonas gingivalis

<400> SEQUENCE: 52

Thr Ile Asp Leu Ser Ala Tyr Ala Gly Gln Gln Val Tyr Leu Ala Phe
1               5                   10                  15

Arg

<210> SEQ ID NO 53
<211> LENGTH: 23
<212> TYPE: PRT
<213> ORGANISM: Porphyromonas gingivalis

<400> SEQUENCE: 53

Leu Tyr Leu Asp Asp Val Ala Val Ser Gly Glu Gly Ser Ser Asn Asp
1               5                   10                  15

Tyr Thr Tyr Thr Val Tyr Arg
            20

<210> SEQ ID NO 54
<211> LENGTH: 8
<212> TYPE: PRT
<213> ORGANISM: Porphyromonas gingivalis

<400> SEQUENCE: 54

Pro Gln Ser Val Trp Ile Glu Arg
1               5

<210> SEQ ID NO 55
<211> LENGTH: 13
<212> TYPE: PRT
<213> ORGANISM: Porphyromonas gingivalis

<400> SEQUENCE: 55

Thr Val Val Thr Ala Pro Glu Ala Ile Arg Gly Thr Arg
1               5                   10

<210> SEQ ID NO 56
<211> LENGTH: 20
<212> TYPE: PRT
<213> ORGANISM: Porphyromonas gingivalis

<400> SEQUENCE: 56

Thr Gly Thr Asn Ala Gly Asp Phe Thr Val Val Phe Glu Glu Thr Pro
1               5                   10                  15

Asn Gly Ile Asn
            20

<210> SEQ ID NO 57
<211> LENGTH: 20
<212> TYPE: PRT
<213> ORGANISM: Porphyromonas gingivalis

<400> SEQUENCE: 57

Tyr Tyr Tyr Ala Val Asn Asp Gly Phe Pro Gly Asp His Tyr Ala Val
1               5                   10                  15

Met Ile Ser Lys
            20

<210> SEQ ID NO 58
<211> LENGTH: 15
<212> TYPE: PRT
<213> ORGANISM: Porphyromonas gingivalis

<400> SEQUENCE: 58

Cys Val Asn Val Thr Val Asn Ser Thr Gln Phe Asn Pro Val Lys
1               5                   10                  15

<210> SEQ ID NO 59
<211> LENGTH: 16
<212> TYPE: PRT
<213> ORGANISM: Porphyromonas gingivalis

<400> SEQUENCE: 59

Lys Cys Val Asn Val Thr Val Asn Ser Thr Gln Phe Asn Pro Val Lys
1               5                   10                  15

<210> SEQ ID NO 60
<211> LENGTH: 8
<212> TYPE: PRT
<213> ORGANISM: Porphyromonas gingivalis

<400> SEQUENCE: 60

Tyr Thr Pro Val Glu Glu Lys Gln
1               5

<210> SEQ ID NO 61
<211> LENGTH: 8
<212> TYPE: PRT
<213> ORGANISM: Porphyromonas gingivalis

<400> SEQUENCE: 61

Ser Gly Gln Ala Glu Ile Val Leu
1               5

<210> SEQ ID NO 62
<211> LENGTH: 8
<212> TYPE: PRT
<213> ORGANISM: Porphyromonas gingivalis

<400> SEQUENCE: 62

Ala Asp Phe Thr Glu Thr Phe Glu
1               5

<210> SEQ ID NO 63
<211> LENGTH: 8
<212> TYPE: PRT
<213> ORGANISM: Porphyromonas gingivalis

<400> SEQUENCE: 63

Ala Asn Glu Ala Lys Val Val Leu
1               5

<210> SEQ ID NO 64
<211> LENGTH: 8
<212> TYPE: PRT
<213> ORGANISM: Porphyromonas gingivalis

<400> SEQUENCE: 64

Asp Val Tyr Thr Asp His Gly Asp
1               5

```
<210> SEQ ID NO 65
<211> LENGTH: 8
<212> TYPE: PRT
<213> ORGANISM: Porphyromonas gingivalis

<400> SEQUENCE: 65

Ala Glu Val Leu Asn Glu Asp Phe
1               5

<210> SEQ ID NO 66
<211> LENGTH: 8
<212> TYPE: PRT
<213> ORGANISM: Porphyromonas gingivalis

<400> SEQUENCE: 66

Thr Val Val Thr Ala Pro Glu Ala
1               5

<210> SEQ ID NO 67
<211> LENGTH: 8
<212> TYPE: PRT
<213> ORGANISM: Porphyromonas gingivalis

<400> SEQUENCE: 67

Gly Gly Pro Lys Thr Ala Pro Ser
1               5

<210> SEQ ID NO 68
<211> LENGTH: 8
<212> TYPE: PRT
<213> ORGANISM: Porphyromonas gingivalis

<400> SEQUENCE: 68

Ala Pro Ala Pro Tyr Gln Glu Arg
1               5

<210> SEQ ID NO 69
<211> LENGTH: 8
<212> TYPE: PRT
<213> ORGANISM: Porphyromonas gingivalis

<400> SEQUENCE: 69

Ala Glu Leu Leu Asn Glu Asp Phe
1               5

<210> SEQ ID NO 70
<211> LENGTH: 7
<212> TYPE: PRT
<213> ORGANISM: Porphyromonas gingivalis

<400> SEQUENCE: 70

Thr Val Val Thr Ala Pro Glu
1               5
```

ANTIGENIC COMPLEX FOR THE DIAGNOSIS AND TREATMENT OF *PORPHYROMONAS GINGIVALIS* INFECTION

FIELD OF INVENTION

This invention relates to a multimeric protein complex from *Porphyronionas gingivalis*. The present invention also provides methods of obtaining the multimeric complex and to pharmaceutical compositions and associated agents based on the complex and components thereof for the detection, prevention and treatment of periodontal disease associated with *P. gingivalis*.

BACKGROUND OF THE INVENTION

Periodontal diseases are bacterial-associated inflammatory diseases of the supporting tissues of the teeth and range from the relatively mild form of gingivitis, the non-specific, reversible inflammation of gingival tissue to the more aggressive forms of periodontitis which are characterised by the destruction of the tooth's supporting structures. Periodontitis is associated with a subgingival infection of a consortium of specific Gram-negative bacteria that leads to the destruction of the periodontium and is a major public health problem. One bacterium that has attracted considerable interest is *P. gingivalis* as the recovery of this microorganism from adult periodontitis lesions can be up to 50% of the subgingival anaerobically cultivable flora, whereas *P. gingivalis* is rarely recovered, and then in low numbers, from healthy sites. A proportional increase in the level of *P. gingivalis* in subgingival plaque has been associated with an increased severity of periodontitis and eradication of the microorganism from the cultivable subgingival microbial population is accompanied by resolution of the disease. The progression of periodontitis lesions in non-human primates has been demonstrated with the subgingival implantation of *P. gingivalis*. These findings in both animals and humans suggest a major role for *P. gingivalis* in the development of adult periodontitis.

*P. gingivalis* is a black-pigmented, anaerobic, asaccharolytic, proteolytic Gram-negative rod that obtains energy from the metabolism of specific amino acids. The microorganism has an absolute growth requirement for iron, preferentially in the form of haeme or its Fe(III) oxidation product haemin and when grown under conditions of excess haemin is highly virulent in experimental animals. A number of virulence factors have been implicated in the pathogenicity of *P. gingivalis* including the capsule, adhesins, cytotoxins and extracellular hydrolytic enzymes. In particular, proteases have received a great deal of attention for their ability to degrade a broad range of host proteins including structural proteins and others involved in defence. The proteins that have been shown to be substrates for *P. gingivalis* proteolytic activity include collagen types I and IV, fibronectin, fibrinogen, laminin, complement and plasma clotting cascade proteins, $\alpha_1$-antitrypsin, $\alpha_2$-macroglobulin, antichymotrypsin, antithrombin III, antiplasmin, cystatin C, IgG and IgA. The major proteolytic activities associated with this organism have been defined by substrate specificity and are "trypsin-like", that is cleavage on the carboxyl side of arginyl and lysyl residues and collagenolytic although other minor activities have been reported.

*P. gingivalis* trypsin-like proteolytic activity has been shown to degrade complement, generating biologically active C5a, impair the phagocytic and other functions of neutrophils by modifying surface receptors, and abrogate the clotting potential of fibrinogen prolonging plasma clotting time. The trypsin-like proteolytic activity of *P. gingivalis* also generates Fc fragments from human IgG1 stimulating the release of pro-inflammatory cytokines from mononuclear cells and is associated with vascular disruption and enhanced vascular permeation through the activation of the kallikrein-kinin cascade. *P. gingivalis* spontaneous mutants with reduced trypsin-like activity as well as wild-type cells treated with the trypsin-like protease inhibitor N-p-tosyl-L-lysine chloromethyl ketone are avirulent in animal models. Further, it has been shown that *P. gingivalis* grown under controlled, haemin-excess conditions expressed more trypsin-like and less collagenolytic activity and were more virulent in mice relative to cells grown under haemin-limited but otherwise identical conditions.

There has been considerable endeavour to purify and characterise the trypsin-like proteases of *P. gingivalis* from cell-free culture fluids. Chen et al, (1992) [J Biol Chem 267: 18896-18901] have purified and characterised a 50 kDa arginine-specific, thiol protease from the culture fluid of *P. gingivalis* H66 designated Arg-gingipain. A similar arginine-specific thiol protease has been disclosed in JP 07135973 and the amino acid sequence disclosed in WO 9507286 and in Kirszbaum et al, 1995 [Biochem Biophys Res Comm 207: 424-431]. Pike et al (1994) [J Biol Chem 269:406-411] have characterised a 60 kDa lysine-specific cysteine proteinase from the culture fluid of *P. gingivalis* H66 designated Lys-gingipain and the partial gene sequence for this enzyme was disclosed in WO 9511298 and fully disclosed in WO 9617936. In addition, a cell surface protein complex of *P. gingivalis* comprising a 300 kDa complex of arginine-specific and lysine-specific proteases both containing adhesin domains is disclosed in U.S. Pat. No. 6,511,666.

SUMMARY OF TILE INVENTION

The present inventors have extracted from *P. gingivalis* a cell surface associated complex) comprising a multimeric complex of processed domains of RgpA, Kgp and HagA to form a high molecular weight (>300 kDa) proteinase-adhesin complex.

Accordingly in a first aspect the present invention consists in a purified multimeric complex from *P. gingivalis*, the complex comprising at least one domain from each of RgpA, Kgp and HagA, and having a molecular weight greater than about 300 kDa.

In a preferred embodiment the complex has a molecular weight greater than about 500 kDa, more preferably more than about 800 kDa.

In a second aspect of the present invention provides a method of obtaining a purified multimeric complex from *P. gingivalis*, the complex comprising at least one domain from each of RgpA, Kgp and HagA, and having a molecular weight greater than about 300 kDa the method comprising detergent extraction of the complex from whole *Porphyromonas gingivalis* cells.

In a preferred embodiment the complex is subjected to further purification using ion exchange or ultrafiltration and diafiltration methods.

In a further preferred embodiment the detergent is Triton X114.

In a preferred embodiment the *Porphyromonas gingivalis* is a virulent strains. It is also preferred that the *P. gingivalis* has high arginine and/or lysine proteolytic activity.

In a third aspect the present invention consists in a composition for use in eliciting an immune response directed against *Porphyromonas gingivalis*, the composition comprising an effective amount of the complex of the first aspect of the present invention and a suitable adjuvant and/or acceptable carrier.

In a fourth aspect the present invention consists in an antibody preparation comprising antibodies specifically directed against the complex of the first aspect of the present invention. The antibodies may be polyclonal antibodies or monoclonal antibodies.

In a fifth aspect the present invention consists in a method of treating a subject suffering from *Porphyromonas gingivalis* infection, the method comprising administering to the subject an amount of the antibody preparation of the fourth aspect of the present invention.

As will be recognised by those skilled in the art the antibody preparation may be administered by any of a number of well known routes, however, it is presently preferred that the preparation is administered orally.

In a sixth aspect the present invention consists in a method of reducing the prospect of *Porphyromonas gingivalis* infection in an individual and/or severity of disease, the method comprising administering to the individual an amount of the composition of the third aspect of the present invention effective to induce an immune response in the individual directed against *Porphyromonas gingivalis*.

In use the antibodies of the fourth aspect of the present invention may be blended into oral compositions such as toothpaste, mouthwash, toothpowders and liquid dentrifices, mouthwashes, trouches, chewing gums, dental pastes, gingival massage creams, gargle tablets, dairy products and other food stuffs.

In another aspect the invention provides a method of diagnosis for the presence of *Porphyromonas gingivalis* characterised by the use of the complex of the first aspect of the present invention or antibody of the fourth aspect of the present invention. These methods will involve known techniques including for example, enzyme linked immunosorbent assay.

The invention also provides diagnostic kits comprising the complex of the first aspect of the present invention or antibody of the fourth aspect of the present invention.

The invention also provides a method of treatment of a patient human and/or animal either suffering from *Porphyromonas gingivalis* infection comprising active vaccination of said patient with a composition according to the third aspect and/or passive vaccination of said patient with an antibody of the fourth aspect of the present invention.

BRIEF DESCRIPTION OF FIGURES

FIG. 3. Diagrammatic representation of RgpA, Kgp and HagA showing the processed proteinase catalytic and adhesin domains and the N-terminal sequences of each domain. Shaded areas represent the mature, processed domains.

DETAILED DESCRIPTION OF THE INVENTION

Figure 1:
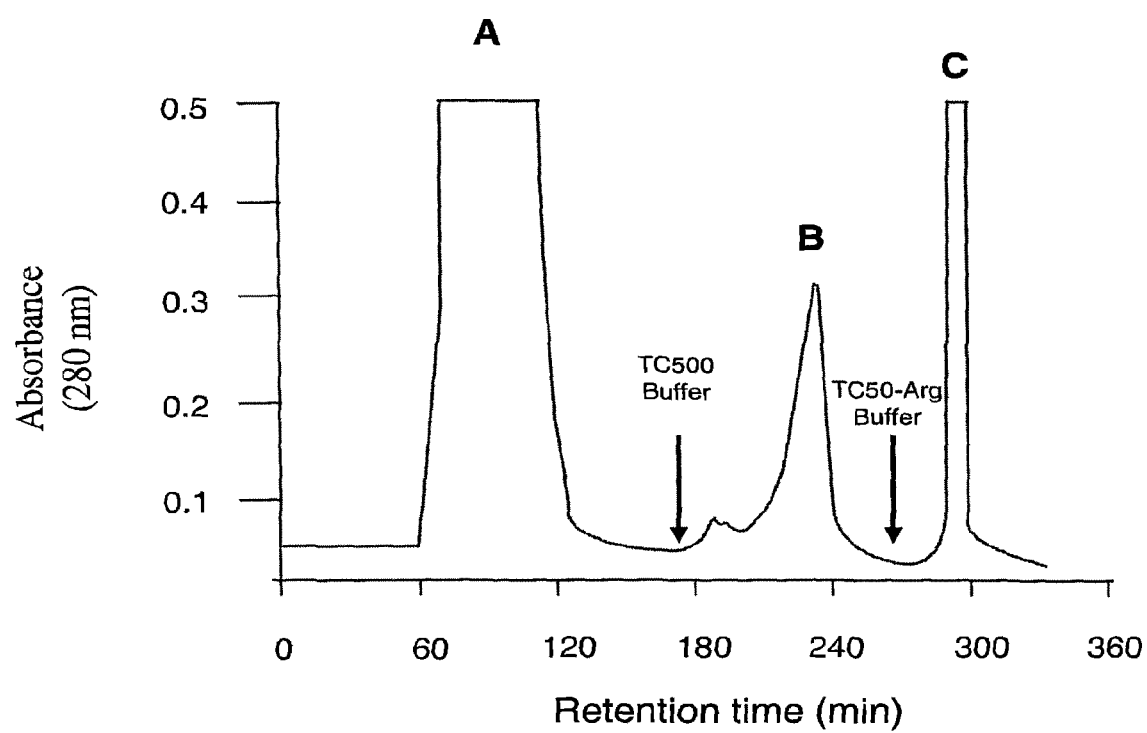
FIG. 1. Arg-Sepharose affinity chromatography of *P. gingivalis* cell Triton X-114 extract. *P. gingivalis* extracts were added to an Arg-Sepharose column and unbound proteins (peak A) were eluted at a flow rate of 1 mL/min. Non-specifically bound proteins (peak B) were eluted with a linear gradient of 0-40% TC 500 buffer (500 mM NaCl, 50 mM Tris/HCl, 5 mM $CaCl_2$, pH 7.4) at a flow rate of 1.0 mL/min. The complex (peak C) was eluted with TC 50-Arg buffer (500 mM arginine, 50 mM NaCl, 50 mM Tris/HCl, 5 mM $CaCl_2$, pH 7.4) at a flow rate of 1 ml/min. The arrows indicate the start of each step gradient.

The intra-oral bacterium *Porphyromonas gingivalis* possesses on its cell surface major trypsin-like proteinases as a >300 kDa multimeric protein complex of Arg-specific and Lys-specific thiol endopeptidases with hemagglutinins (adhesins) herein designated the RgpA-Kgp-HagA complex or antigenic complex. The antigenic complex can be purified from *P. gingivalis* cells by detergent extraction or ultrasonication followed by ultrafiltration/diafiltration or anion exchange and Lys-sepharose or Arg-sepharose chromatography. The extracted and purified complex is a >300 kDa multimeric protein aggregate.

The >300 kDa RgpA-Kgp-HagA proteinase-adhesin complex is referred to herein as the "antigenic complex". It is believed that the antigenic complex contains unique epitopes not displayed on the individual domains or processed proteins. The previously disclosed arginine-specific and lysine-specific thiol proteases discussed above do not exhibit a number of the features of the "antigenic complex" and have proven of limited application to date. However, in experiments conducted to date the antigenic complex has shown characteristics required for development of diagnostic and immunoprophylactic products. The cell surface extracted antigenic complex is accordingly of particular interest for diagnostics and neutralisation by passive immunity through oral compositions containing neutralising antibodies and by vaccine development.

Accordingly in a first aspect the present invention consists in a purified multimeric complex from *P. gingivalis*, the complex comprising at least one domain from each of RgpA, Kgp and HagA, and having a molecular weight greater than about 300 kDa.

In a preferred embodiment the complex has a molecular weight greater than about 500 kDa, more preferably more than about 800 kDa.

RgpA comprises the domains $RgpA_{cat}$, $RgpA_{A1}$, $RgpA_{A2}$ and $RgpA_{A3}$; Kgp comprises the domains $Kgp_{cat}$, $Kgp_{A1}$ and $Kgp_{A2}$ and HagA comprises the domains $HagA_{A1*}$, $HagA_{A1**}$, $HagA_{A2}$ and $HagA_{A3}$. The sequence of these polyproteins and the locations of the domains in a type strain of *P. gingivalis* is as follows:

RgpA polyprotein from *Porphyromonas gingivalis*.
Accession number; AAC18876.
RgpA protein domains.

| RgpA domain | Residues (numbered from the initial methionine) |
|---|---|
| $RgpA_{cat}$ | 228-688 |
| $RgpA_{A1}$ | 720-1081 |
| $RgpA_{A2}$ | 1139-1257 |
| $RgpA_{A3}$ | 1274-1404 |
| $RgpA_{A4}$ | 1432-1706 |

RgpA protein sequence:

(SEQ ID No: 1)

```
   1 MKNLNKFVSI ALCSSLLGGM AFAQQTELGR NPNVRLLEST QQSVTKVQFR MDNLKFTEVQ

61 TPKGIGQVPT YTEGVNLSEK GMPTLPILSR SLAVSDTREM KVEVVSSKFI EKKNVLIAPS

121 KGMIMRNEDP KKIPYVYGKT YSQNKFFPGE IATLDDPFIL RDVRGQVVNF APLQYNPVTK

181 TLRIYTEITV AVSETSEQGK NILNKKGTFA GFEDTYKRMF MNYEPGRYTP VEEKQNGRMI

241 VIVAKKYEGD IKDFVDWKNQ RGLRTEVKVA EDIASPVTAN AIQQFVKQEY EKEGNDLTYV

301 LLIGDHKDIP AKITPGIKSD QVYGQIVGND HYNEVFIGRF SCESKEDLKT QIDRTIHYER

361 NITTEDKWLG QALCIASAEG GPSADNGESD IQHENVIANL LTQYGYTKII KCYDPGVTPK

421 NIIDAFNGGI SLANYTGHGS ETAWGTSHFG TTHVKQLTNS NQLPFIFDVA CVNGDFLFSM

481 PCFAEALMRA QKDGKPTGTV AIIASTINQS WASPMRGQDE MNEILCEKHP NNIKRTFGGV

541 TMNGMFAMVE KYKKDGEKML DTWTVFGDPS LLVRTLVPTK MQVTAPAQIN LTDASVNVSC

601 DYNGAIATIS ANGKMFGSAV VENGTATINL TGLTNESTLT LTVVGYNKET VIKTINTNGE

661 PNPYQPVSNL TATTQGQKVT LKWDAPSTKT NATTNTARSV DGIRELVLLS VSDAPELLRS

721 GQAEIVLEAH DVWNDGSGYQ ILLDADHDQY GQVIPSDTHT LWPNCSVPAN LFAPFEYTVP

781 ENADPSCSPT NMIMDGTASV NIPAGTYDFA IAAPQANAKI WIAGQGPTKE DDYVFEAGKK

841 YHFLMKKMGS GDGTELTISE GGGSDYTYTV YRDGTKIKEG LTATTFEEDG VATGNHEYCV

901 EVKYTAGVSP KVCKDVTVEG SNEFAPVQNL TGSAVGQKVT LKWDAPNGTP NPNPNPNPNP

961 NPGTTTLSES FENGIPASWK TIDADGDGHG WKPGNAPGIA GYNSNGCVYS ESFGLGGIGV

1021 LTPDNYLITP ALDLPNGGKL TFWVCAQDAN YASEHYAVYA SSTGNDASNF TNALLEETIT

1081 AKGVRSPEAM RGRIQGTWRQ KTVDLPAGTK YVAFRHFQST DMFYIDLDEV EIKANGKRAD

1141 FTETFESSTH GEAPAEWTTI DADGDGQGWL CLSSGQLDWL TAHGGTNVVS SFSWNGMALN

1201 PDNYLISKDV TGATKVKYYY AVNDGFPGDH YAVMISKTGT NAGDFTVVFE ETPNGINKGG

1261 ARFGLSTEAD GAKPQSVWIE RTVDLPAGTK YVAFRHYNCS DLNYILLDDI QFTMGGSPTP
```

```
1321 TDYTYTVYRD GTKIKEGLTE TTFEEDGVAT GNHEYCVEVK YTAGVSPKKC VNVTVNSTQF

1381 NPVKNLKAQP DGGDVVLKWE APSAKKTEGS REVKRIGDGL FVTIEPANDV RANEAKVVLA

1441 ADNVWGDNTG YQFLLDADHN TFGSVIPATG PLFTGTASSD LYSANFESLI PANADPVVTT

1501 QNIIVTGQGE VVIPGGVYDY CITNPEPASG KMWIAGDGGN QPARYDDFTF EAGKKYTFTM

1561 RRAGMGDGTD MEVEDDSPAS YTYTVYRDGT KIKEGLTETT YRDAGMSAQS HEYCVEVKYT

1621 AGVSPKVCVD YIPDGVADVT AQKPYTLTVV GKTITVTCQG EAMIYDMNGR RLAAGRNTVV

1681 YTAQGGYYAV MVVVDGKSYV EKLAIK
```

Kgp Polyprotein from *Porphyromonas gingivalis*.
Accession number; AAB60809.
Kgp protein domains.

| Kgp domain | Residues (numbered from the initial methionine) |
|---|---|
| Kgp$_{cat}$ | 229-710 |
| Kgp$_{A1}$ | 738-1099 |
| Kgp$_{A2}$ | 1157-1275 |
| Kgp$_{A3}$ | 1292-1424 |
| Kgp$_{A4}$ | 1427-1546 |
| Kgp$_{A5}$ | 1548-1732 |

Kgp protein sequence:

```
                                                                    (SEQ ID No: 2)
   1 MRKLLLLIAA SLLGVGLYAQ SAKIKLDAPT TRTTCTNNSF KQFDASFSFN EVELTKVETK

61 GGTFASVSIP GAFPTGEVGS PEVPAVRKLI AVPVGATPVV RVKSFTEQVY SLNQYGSEKL

121 MPHQPSMSKS DDPEKVPFVY NAAAYARKGF VGQELTQVEM LGTMRGVRIA ALTINPVQYD

181 VVANQLKVRN NIEIEVSFQG ADEVATQRLY DASFSPYFET AYKQLFNRDV YTDHGDLYNT

241 PVRMLVVAGA KFKEALKPWL TWKAQKGFYL DVHYTDEAEV GTTNASIKAF IHKKYNDGLA

301 ASAAPVFLAL VGDTDVISGE KGKKTKKVTD LYYSAVDGDY FPEMYTFRMS ASSPEELTNI

361 IDKVLMYEKA TMPDKSYLEK VLLIAGADYS WNSQVGQPTI KYGMQYYYNQ EHGYTDVYNY

421 LKAPYTGCYS HLNTGVSFAN YTAHGSETAW ADPLLTTSQL KALTNKDKYF LAIGNCCITA

481 QFDYVQPCFG EVITRVKEKG AYAYIGSSPN SYWGEDYYWS VGANAVFGVQ PTFEGTSMGS

541 YDATFLEDSY NTVNSIMWAG NLAATHAGNI GNITHIGAHY YWEAYHVLGD GSVMPYRAMP

601 KTNTYTLPAS LPQNQASYSI QASAGSYVAI SKDGVLYGTG VANASGVATV SMTKQITENG

661 NYDVVITRSN YLPVIKQIQV GEPSPYQPVS NLTATTQGQK VTLKWEAPSA KKAEGSREVK

721 RIGDGLFVTI EPANDVRANE AKVVLAADNV WGDNTGYQFL LDADHNTFGS VIPATGPLFT

781 GTASSNLYSA NFEYLIPANA DPVVTTQNII VTGQGEVVIP GGVYDYCITN PEPASGKMWI

841 AGDGGNQPAR YDDFTFEAGK KYTFTMRRAG MGDGTDMEVE DDSPASYTYT VYRDGTKIKE

901 GLTATTFEED GVAAGNHEYC VEVKYTAGVS PKVCKDVTVE GSNEFAPVQN LTGSSVGQKV

961 TLKWDAPNGT PNPNPNPNPN PGTTLSESFE NGIPASWKTI DADGDGHGWK PGNAPGIAGY

1021 NSNGCVYSES FGLGGIGVLT PDNYLITPAL DLPNGGKLTF WVCAQDANYA SEHYAVYASS

1081 TGNDASNFTN ALLEETITAK GVRSPKAIRG RIQGTWRQKT VDLPAGTKYV AFRHFQSTDM

1141 FYIDLDEVEI KANGKRADFT ETFESSTHGE APAEWTTIDA DGDGQGWLCL SSGQLDWLTA

1201 HGGSNVVSSF SWNGMALNPD NYLISKDVTG ATKVKYYYAV NDGFPGDHYA VMISKTGTNA

1261 GDFTVVFEET PNGINKGGAR FGLSTEANGA KPQSVWIERT VDLPAGTKYV AFRHYNCSDL

1321 NYILLDDIQF TMGGSPTPTD YTYTVYRDGT KIKEGLTETT FEEDGVATGN HEYCVEVKYT

1381 AGVSPKKCVN VTVNSTQFNP VQNLTAEQAP NSMDAILKWN APASKRAEVL NEDFENGIPA

1441 SWKTIDADGD GNNWTTTPPP GGSSFAGHNS AICVSSASYI NFEGPQNPDN YLVTPELSLP
```

```
-continued
1501 GGGTLTFWVC AQDANYASEH YAVYASSTGN DASNFANALL EEVLTAKTVV TAPEAIRGTR

1561 AQGTWYQKTV QLPAGTKYVA FRHFGCTDFF WINLDDVVIT SGNAPSYTYT IYRNNTQIAS

1621 GVTETTYRDP DLATGFYTYG VKVVYPNGES AIETATLNIT SLADVTAQKP YTLTVVGKTI

1681 TVTCQGEAMI YDMNGRRLAA GRNTVVYTAQ GGHYAVMVVV DGKSYVEKLA VK
```

HagA Polyprotein from *Porphyromonas gingivalis*. Accession number; P59915.
HagA protein domains.

| HagA domain | Residues (numbered from the initial methionine) |
| --- | --- |
| HagA$_{41}$ | 26-351 |
| HagA$_{41}$* | 366-625 |
| HagA$_{41}$** | 820-1077 and 1272-1529 |
| HagA$_{42}$ | 685-803 and 1137-1255 and 1589-1707 |
| HagA$_{43}$ | 1724-1856 |
| HagA$_{44}$ | 1859-1978 |
| HagA$_{45}$ | 1980-2164 |

HagA protein sequence:

(SEQ ID No: 3)
```
   1 MRKLNSLFSL AVLLSLLCWG QTAAAQGGPK TAPSVTHQAV QKGIRTSKAK DLRDPIPAGM

61 ARIILEAHDV WEDGTGYQML WDADHNQYGA SIPEESFWFA NGTIPAGLYD PFEYKVPVNA

121 DASFSPTNFV LDGTASADIP AGTYDYVIIN PNPGIIYIVG EGVSKGNDYV VEAGKTYHFT

181 VQRQGPGDAA SVVVTGEGGN EFAPVQNLQW SVSGQTVTLT WQAPASDKRT YVLNESFDTQ

241 TLPNGWTMID ADGDGHNWLS TINVYNTATH TGDGAMFSKS WTASSGAKID LSPDNYLVTP

301 KFTVPENGKL SYWVSSQEPW TNEHYGVFLS TTGNEAANFT IKLLEETLGS GKPAPMNLVK

361 SEGVKAPAPY QERTIDLSAY AGQQVYLAFR HFGCTGIFRL YLDDVAVSGE GSSNDYTYTV

421 YRDNVVIAQN LTATTFNQEN VAPGQYNYCV EVKYTAGVSP KVCKDVTVEG SNEFAPVQNL

481 TGSAVGQKVT LKWDAPNGTP NPNPGTTTLS ESFENGIPAS WKTIDADGDG NNWTTTPPPG

541 GSSFAGHNSA ICVSSASYIN FEGPQNPDNY LVTPELSLPN GGTLTFWVCA QDANYASEHY

601 AVYASSTGND ASNFANALLE EVLTAKTVVT APEAIRGTRV QGTWYQKTVQ LPAGTKYVAF

661 RHFGCTDFFW INLDDVEIKA NGKRADFTET FESSTHGEAP AEWTTIDADG DGQGWLCLSS

721 GQLGWLTAHG GTNVVASFSW NGMALNPDNY LISKDVTGAT KVKYYYAVND GFPGDHYAVM

781 ISKTGTNAGD FTVVFEETPN GINKGGARFG LSTEANGAKP QSVWIERTVD LPAGTKYVAF

841 RHYNCSDLNY ILLDDIQFTM GGSPTPTDYT YTVYRDGTKI KEGLTETTFE EDGVATGNHE

901 YCVEVKYTAG VSPKECVNVT VDPVQFNPVQ NLTGSAVGQK VTLKWDAPNG TPNPNPGTTT

961 LSESFENGIP ASWKTIDADG DGNNWTTTPP PGGTSFAGHN SAICVSSASY INFEGPQNPD

1021 NYLVTPELSL PNGGTLTFWV CAQDANYASE HYAVYASSTG NDASNFANAL LEEVLTAKTV

1081 VTAPEAIRGT RVQGTWYQKT VQLPAGTKYV AFRHFGCTDF FWINLDDVEI KANGKRADFT

1141 ETFESSTHGE APAEWTTIDA DGDGQGWLCL SSGQLDWLTA HGGTNVVASF SWNGMALNPD

1201 NYLISKDVTG ATKVKYYYAV NDGFPGDHYA VMISKTGTNA GDFTVVFEET PNGINKGGAR

1261 FGLSTEANGA KPQSVWIERT VDLPAGTKYV AFRHYNCSDL NYILLDDIQF TMGGSPTPTD

1321 YTYTVYRDGT KIKEGLTETT FEEDGVATGN HEYCVEVKYT AGVSPKECVN VTVDPVQFNP

1381 VQNLTGSAVG QKVTLKWDAP NGTPNPNPGT TTLSESFENG IPASWKTIDA DGDGNNWTTT

1441 PPPGGTSFAG HNSAICVSSA SYINFEGPQN PDNYLVTPEL SLPNGGTLTF WVCAQDANYA

1501 SEHYAVYASS TGNDASNFAN ALLEEVLTAK TVVTAPEAIR GTRVQGTWYQ KTVQLPAGTK

1561 YVAFRHFGCT DFFWINLDDV EIKANGKRAD FTETFESSTH GEAPAEWTTI DADGDGQGWL

1621 CLSSGQLGWL TAHGGTNVVA SFSWNGMALN PDNYLISKDV TGATKVKYYY AVNDGFPGDH
```

```
                            -continued
1681 YAVMISKTGT NAGDFTVVFE ETPNGINKGG ARFGLSTEAN GAKPQSVWIE RTVDLPAGTK

1741 YVAFRHYNCS DLNYILLDDI QFTMGGSPTP TDYTYTVYRD GTKIKEGLTE TTFEEDGVAT

1801 GNHEYCVEVK YTAGVSPKEC VNVTINPTQF NPVQNLTAEQ APNSMDAILK WNAPASKRAE

1861 VLNEDFENGI PASWKTIDAD GDGNNWTTTP PPGGSSFAGH NSAICVSSAS YINFEGPQNP

1921 DNYLVTPELS LPGGGTLTFW VCAQDANYAS EHYAVYASST GNDASNFANA LLEEVLTAKT

1981 VVTAPEAIRG TRVQGTWYQK TVQLPAGTKY VAFRHFGCTD FFWINLDDVV ITSGNAPSYT

2041 YTIYRNNTQI ASGVTETTYR DPDLATGFYT YGVKVVYPNG ESAIETATLN ITSLADVTAQ

2101 KPYTLTVVGK TITVTCQGEA MIYDMNGRRL AAGRNTVVYT AQGGHYAVMV VVDGKSYVEK

2161 LAVK
```

In a preferred embodiment at least seven proteins are present in the complex. In a preferred embodiment these proteins are selected from the group consisting of $Kgp_{cat}$, $RgpA_{cat}$, $RgPA_{A1}$, $Kgp_{A1}$, $RgPA_{A3}$, $KgpA_3$, $HagA_{A3}$, $HagA_{A1**}$, $RgpA_{A2}$, $Kgp_{A2}$, $HagA_{A2}$ and $HagA_{A1}$.

As the purified antigenic complex normally has enzymatic activity it is preferred in a number of uses the thiol proteinases are rendered inactive. This may be achieved in a number of ways, for example by oxidation, mutation or by small molecular weight inhibitors. It is presently preferred that inactivation is by oxidation.

As used herein the term "purified" means that the antigenic complex has been removed from its natural surrounds in that the antigenic complex is substantially free of P. gingivalis cells.

As will be understood by those skilled in this field in order for the antigenic complex to have the preferred molecular weight the antigenic complex is made up of multiple copies of various domains from RgpA, KgpA and HagA. It is believed that the antigenic complex has a core molecular weight of about 223 to about 294 kDa which forms large aggregates >300 kDa.

The antigenic complex can be used to generate antibodies using standard techniques. The animals used for antibody generation can be rabbits, goats, chickens, sheep, horses, cows etc. When a high antibody titre against the complex is detected by immunoassay the animals are bled or eggs or milk are collected and the serum prepared and/or antibody purified using standard techniques or monoclonal antibodies produced by fusing spleen cells with myeloma cells using standard techniques. The antibody (immunoglobulin fraction) may be separated from the culture or ascites fluid, serum, milk or egg by salting out, gel filtration, ion exchange and/or affinity chromatography, and the like, with salting out being preferred. In the salting out method the antiserum or the milk is saturated with ammonium sulphate to produce a precipitate, followed by dialyzing the precipitate against physiological saline to obtain the purified immunoglobulin fraction with the specific anti-complex antibodies. The preferred antibody is obtained from the equine antiserum and the bovine antiserum and milk. In this invention the antibody contained in the antiserum and milk obtained by immunising the animal with the inactivated complex is blended into the oral composition. In this case the antiserum and milk as well as the antibody separated and purified from the antiserum and milk may be used. Each of these materials may be used alone or in combination of two or more. Antibodies against the complex can be used in oral compositions such as toothpaste and mouthwash to neutralise the complex and thus prevent disease. The anti-complex antibodies can also be used for the early detection of P. gingivalis in subgingival plaque samples by a chair-side Enzyme Linked Immunosorbent Assay (ELISA).

For oral compositions it is preferred that the amount of the above antibodies administered is 0.0001-50 g/kg/day and that the content of the above antibodies is 0.0002-10% by weight preferably 0.002-5% by weight of the composition. The oral composition of this invention which contains the above-mentioned serum or milk antibody may be prepared and used in various forms applicable to the mouth such as dentifrice including toothpastes, toothpowders and liquid dentifrices, mouthwashes, troches, periodontal pocket irrigating devices, chewing gums, dental pastes, gingival massage creams, gargle tablets, dairy products and other foodstuffs. The oral composition according to this invention may further include additional well known ingredients depending on the type and form of a particular oral composition.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 4.5 to about 9 and typically from about 5.5 to 8. The pH is preferably in the range of from about 6 to about 8.0, preferably 7.4. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

Other desirable forms of this invention, the oral composition may be substantially solid or pasty in character, such as toothpowder, a dental tablet or a dentifrice, that is a toothpaste (dental) cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminium silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50,000 $cm^2$/gm, silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal alumino-silicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouthrinse will have a label describing it, in substance, as a mouthrinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, nonionic or ampholytic in nature which does not denature the antibody of the invention, and it is preferred to employ as the surface-active agent a detersive material which imparts to the composition detersive and foaming properties while not denaturing the antibody. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since) these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants suitable for use with antibodies are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.1-5% by weight. It is noteworthy, that the surface active agent may assist in the dissolving of the antibody of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH of about 4.5 to about 9, generally about 5.5 to about 8, preferably about 6 to 8, for at least 2 weeks up to 8 weeks or more up to a lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticizers or softeners, sugar or other sweeteners or such as glucose, sorbitol and the like.

The composition of this invention also includes targeted delivery vehicles such as periodontal pocket irrigation devices, collagen, elastin, or synthetic sponges, membranes or fibres placed in the periodontal pocket or used as a barrier membrane or applied directly to the tooth root.

Another important form of the invention is a vaccine based on the inactivated complex and suitable adjuvant delivered by nasal spray, orally or by injection to produce a specific immune response against the complex thereby reducing colonisation of *P. gingivalis* and neutralising the complex thereby preventing disease. A vaccine can also be based upon a recombinant component of the complex incorporated into an appropriate vector and expressed in a suitable transformed host (eg. *E. coli, Bacillus subtilis, Saccharomyces cerevisiae*, COS cells, CHO cells and HeLa cells) containing the vector. Unlike whole *P. gingivalis* cells or other previously prepared antigens based on fimbriae or the capsule the complex is a safe and effective antigens for the preparation of a composition for use in the prevention of *P. gingivalis*-associated periodontal disease. The complex can be produced using recombinant DNA methods as illustrated herein, or can be synthesized chemically from the amino acid sequence disclosed in the present invention. Additionally, according to the present invention, the complex may be used to generate *P. gingivalis* antisera useful for passive immunization against periodontal disease and infections caused by *P. gingivalis*.

Various adjuvants are used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freunds adjuvant (WA), Adjuvant 65 (containing peanut oil, mannide monooleate and aluminium monostrearate), oil emulsions, Ribi adjuvant, the pluronic polyols, polyamines, Avridine, Quil A, saponin, MPL, QS-21, and mineral gels such as aluminium salts. Other examples include oil in water emulsions such as SAF-1, SAF-0, MF59, Seppic ISA720, and other particulate adjuvants such as ISCOMs and ISCOM matrix. An extensive but exhaustive list of other examples of adjuvants are listed in Cox and Coulter 1992 [In: Wong W K (ed.) *Animals parasite control utilising technology*. Bocca Raton; CRC press, 1992; 49-112]. In addition to the adjuvant the vaccine may include conventional pharmaceutically acceptable carriers, excipients, fillers, buffers or diluents as appropriate. One or more doses of the vaccine containing adjuvant may be administered prophylactically to prevent periodontitis or therapeutically to treat already present periodontitis.

In another preferred composition the preparation is combined with a mucosal adjuvant and administered via the oral or nasal route. Examples of mucosal adjuvants axe cholera toxin and heat labile *E. coli* toxin, the non-toxic B sub-units of these toxins, genetic mutants of these toxins which have reduced toxicity. Other methods which may be utilised to deliver the complex orally or nasally include incorporation of the complex into particles of biodegradable polymers (such as acrylates or polyesters) by micro-encapsulation to aid uptake of the microspheres from the gastrointestinal tract or nasal cavity and to protect degradation of the proteins. Liposomes, ISCOMs, hydrogels are examples of other potential methods which may be further enhanced by the incorporation of targeting molecules such as LTB, CTB or lectins (mannan, chitin, and chitosan) for delivery of the complex to the mucosal immune system. In addition to the vaccine and the mucosal adjuvant or delivery system the vaccine may include conventional pharmaceutically acceptable carriers, excipients, fillers, coatings, dispersion media, antibacterial and antifungal agents, buffers or diluents as appropriate.

Another mode of this embodiment provides for either, a live recombinant viral vaccine, recombinant bacterial vaccine, recombinant attenuated bacterial vaccine, or an inactivated recombinant viral vaccine which is used to protect against infections caused by *P. gingivalis*. Vaccinia virus is the best known example, in the art, of an infectious virus that is engineered to express vaccine antigens derived from other organisms. The recombinant live vaccinia virus, which is attenuated or otherwise treated so that it does not caused disease by itself, is used to immunise the host. Subsequent replication of the recombinant virus within the host provides a continual stimulation of the immune system with the vaccine antigens such as the antigenic complex, thereby providing long lasting immunity.

Other live vaccine vectors include: adenovirus, cytomegalovirus, and preferably the poxviruses such as vaccinia (Paoletti and Panicali, U.S. Pat. No. 4,603,112) and attenuated salmonella strains (Stocker et al., U.S. Pat. Nos. 5,210,035; 4,837,151; and 4,735,801; and Curtis et al., 1988, Vaccine 6: 155-160). Live vaccines are particularly advantageous because they continually stimulate the immune system which can confer substantially long-lasting immunity. When the immune response is protective against subsequent *P. gingivalis* infection, the live vaccine itself may be used in a protective vaccine against *P. gingivalis*. In particular, the live vaccine can be based on a bacterium that is a commensal inhabitant of the oral cavity. This bacterium can be transformed with a vector carrying a recombinant inactivated complex and then used to colonise the oral cavity, in particular the oral mucosa. Once colonised the oral mucosa, the expression of the recombinant protein will stimulate the mucosal associated lymphoid tissue to produce neutralising antibodies. For example, using molecular biological techniques the genes encoding the complex may be inserted into the vaccinia virus genomic DNA at a site which allows for expression of epitopes but does not negatively affect the growth or replication of the vaccinia virus vector. The resultant recombinant virus can be used as the immunogen in a vaccine formulation. The same methods can be used to construct an inactivated recombinant viral vaccine formulation except the recombinant virus is inactivated, such as by chemical means known in the art, prior to use as an immunogen and without substantially affecting the immunogenicity of the expressed immunogen.

As an alternative to active immunisation, immunisation may be passive, i.e. immunisation comprising administration of purified immunoglobulin containing antibody against the complex.

In the context of this disclosure, the terms "adhesin" and "hemagglutinin" may be considered to be synonymous.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In order that the nature of the present invention may be more clearly understood preferred forms thereof will now be described with reference to the following Examples.

Example 1

(1) Preparation of Antigenic Complex

A. Triton X-114 Extraction and Affinity Chromatography.

*Porphyromonas gingivalis* was grown in an anaerobic chamber (MK3 anaerobic workstation; Don Whitley Scientific Ltd., Shipley, England) at 37° C. on horse blood agar plates supplemented with 10% (v/v) lysed horse blood. Bacterial colonies were used to inoculate brain heart infusion media containing 5 µg/ml of hemin and 0.5 µg/ml of cysteine for batch culture growth. Batch culture growth was monitored at 650 nm using a spectrophotometer (Perkin-Elmer model 295E). Culture purity was routinely checked by Gram stain, microscopic examination and using a variety of biochemical tests. Stocks were maintained as lyophilised cultures. *P. gingivalis* cells (2 L) were grown to late exponential phase and harvested by centrifugation (7500 g, 30 min, 4° C.) and washed twice with PG buffer (50 mM Tris-HCl, 150 mM NaCl, 5 mM $CaCl_2$, and 5 mM cysteine-HCl, pH 8.0) in the anaerobic workstation. Cells were resuspended in PG buffer, total volume 60 mL, containing 0.5% v/v Triton X114 and gently mixed at either (a) room temperature for 45 min or (b) 4° C. overnight. For comparison cells were resuspended in PG buffer, total volume 60 mL and subjected to mild sonication using a Branson sonifier 250 with an output control of 3 and a 50% duty cycle. The cell extract was centrifuged (7500 g, 30 min, 4° C.) and the collected supernatant centrifuged (40,000 g, 30 min, 4° C.). The supernatant was then filtered (0.2 µm) and the complex purified by arginine affinity chromatography. Fast protein liquid chromatography (FPLC) was performed at room temperature at a flow rate of 1.0 mL/min. *P. gingivalis* cell supernatant was applied to an Arg-Sepharose column (Hiload XK16/10Q, Pharmacia), installed in a Pharmacia GP-250 FPLC system, in TC 50 buffer (buffer A) (50 mM Tris/HCl, 50 mM NaCl, 5 mM $CaCl_2$, pH 7.4) at a flow rate of 1 mL/min. Non-specifically bound proteins were eluted with a linear gradient of 0-40% TC 50 buffer containing, 500 mM NaCl, 50 mM Tris/HCl, 5 mM $CaCl_2$, pH 7.4 (buffer B) at a flow rate of 1.0 mL/min. The) column was re-equilibrated with buffer A and bound proteins eluted with TC 50 buffer containing 500 mM arginine, pH 7.4 at a flow rate of 1 mL/min. The eluent was monitored at 280 nm. All fractions were collected at 4° C. and stored at −70° C. before further processing. A typical affinity chromatogram of the complex is shown in FIG. 1. Arginine eluted FPLC fractions were concentrated using Vivaspin 20 concentrator (10,000 MWCO) (Sartorius, NSW, Australia) by centrifugation at 3000×g for 15 min periods at 4° C. until the eluant was reduced to a volume of approximately 1 mL. The filter membrane of the Vivaspin 20-concentrator was then rinsed with 1 mL of TC 50 buffer. This procedure purifies and inactivates by oxidation the complex which is then stored frozen (−70° C.) and used as an immunogen.

Benzoyl-L-Arg-p-nitroanilide (Bz-L-Arg-pNA) Sigma, NSW, Australia) and benzyloxycarbonyl-L-Lys-p-nitroanilide (z-L-Lys-p-NA) (Novabiochem, NSW, Australia) were used to assay FPLC fractions for Arg- and Lys proteolytic activity, respectively. Samples of each chromatographic fraction were diluted in TC 150 buffer (total volume of 360 µL) and incubated for 10 minutes at 37° C. with 40 µL, of 100 mM cysteine, pH 8. After incubation, 400 µL of either Bz-L-Arg-pNA or z-L-Lys-p-NA substrate [2 mM Bz-L-Arg-pNA or 2 mM z-L-Lys-p-NA dissolved in 3 mL isopropan-2-ol and mixed with 7 ml of enzyme buffer (400 mM Tris-HCl, 100 mM NaCl and 20 mM cysteine), pH 8] was added and the proteolytic activity determined by measuring the absorbance at 410 nm using a diode Array spectrophotometer (model 8452A, Hewlett Packard, Germany) over 3 minutes. The proteolytic activity is expressed in U, where U-µmol substrate converted $min^1$ at 37° C. The protein concentration of FPLC fractions and purified samples was determined using the Bradford protein assay (BioRad) with BSA as a standard. The protein concentration and proteolytic activity of the complex extracted via the Triton X114 method or sonication method and purified by affinity chromatography is shown in Table 1. The Triton X114 extraction method produced the antigenic complex in a higher yield and higher purity compared to the traditional sonication method, Table 1.

TABLE 1

Purification of the antigenic complex using Triton X114 and sonication methodologies.

| | Protein | Arg Proteolytic activity | Lys Proteolytic activity | Arg Proteolytic activity | Lys Proteolytic activity | Purification (-fold) | |
|---|---|---|---|---|---|---|---|
| | (mg) | (U)* | (U)# | (U mg$^{-1}$) | (U mg$^{-1}$) | Arg | Lys |
| Crude cell sonicate^ | 10.34 ± 2.52 | 13.60 ± 2.30 | 1.89 ± 0.78 | 1.30 ± 0.62 | 0.18 ± 0.09 | 1 | 1 |
| Complex Purified from the cell sonicate | 0.72 ± 0.15 | 1.23 ± 0.24 | 0.09 ± 0.02 | 1.72 ± 0.84 | 0.12 ± 0.06 | 1.3 | 0.68 |
| Crude Triton X114 extract^ | 70.14 ± 9.23 | 35.62 ± 4.32 | 4.56 ± 1.35 | 0.51 ± 0.22 | 0.07 ± 0.01 | 1 | 1 |
| Antigenic Complex Purified from the Triton X114 extract | 0.63 ± 0.12 | 2.45 ± 0.68 | 1.19 ± 0.86 | 4.11 ± 1.40 | 1.97 ± 0.56 | 8.16 | 30.35 |

*Amidolytic activity using 2.0 mM Bz-L-Arg-pNA: 1 unit (U) = 1 μmol min-1 at 37° C.
Amidolytic activity using 2.0 mM z-L-Lys-pNA: 1 unit (U) = 1 μmol min-1 at 37° C.
^330 ml of TX-114 treated and sonicated *P. gingivalis* extracts were used for complex purification.

Figure 2:
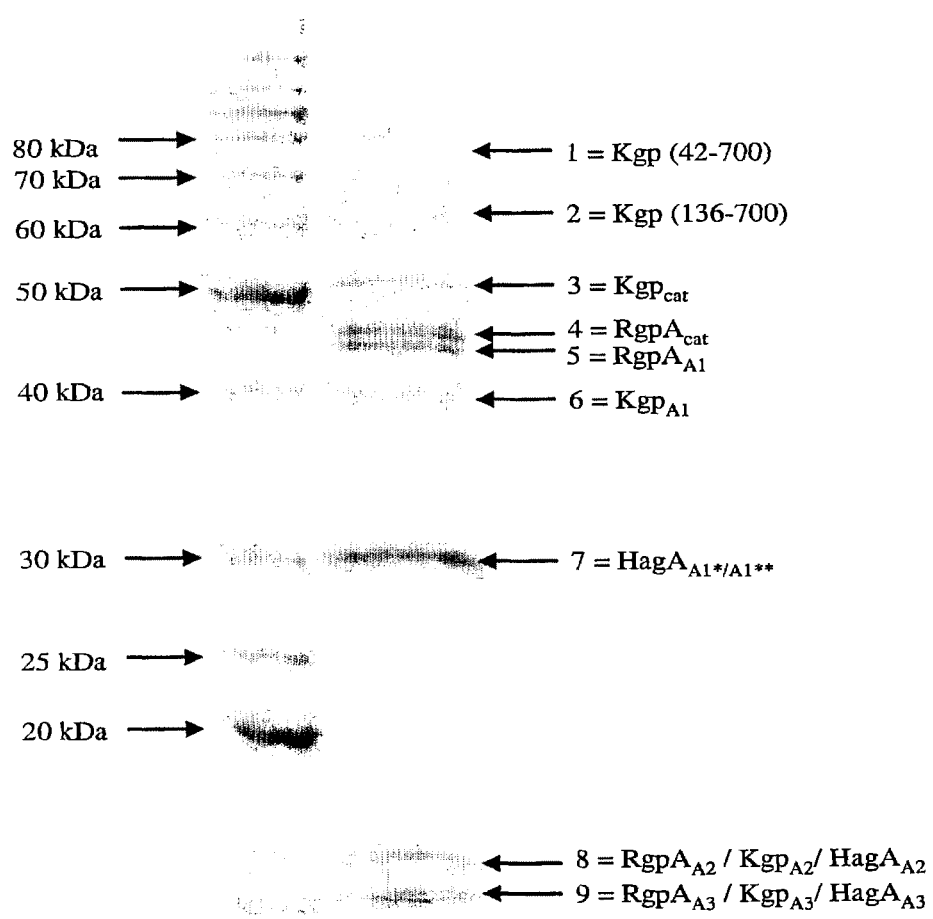
FIG. 2. SDS-PAGE of Mg-affinity purified *P. gingivalis* Triton X114 extracted complex. Lane 1, Invitrogen molecular weight standards (kDa); lane 2, Triton X114 extracted complex. Gels stained with Coomassie blue. Protein bands (1 to 9) were excised or transferred onto PVDF membrane and identified by peptide mass finger printing analysis or N-terminal sequence analysis, respectively, as described.

Sodium Dodecyl Sulphate-Polyacrylamide Gel Electrophoresis (SDS-PAGE) was performed on FPLC fractions by using a Novex™ electrophoresis system (Novex, San Diego, Calif.) with Novex 12% Tris-glycine pre-cast mini gels (Invitrogen, NSW, Australia). RgpA-Kgp complex proteins samples (20 μg) were precipitated by addition of trichloroacetic acid (TCA) to a final concentration of 10% v/v and incubated for 20 min at 4° C. Precipitated proteins were collected by centrifugation (10 min, 13,000 g) and re-suspended in 20 μl of reducing sample buffer (10% w/v SDS, 0.05% w/v bromophenol blue, 25% v/v glycerol and 0.05% v/v 2-Mercaptoehtanol) and the pH adjusted with the addition of 10 μL of 1.5 M Tris/HCl, pH 8.0 and then heated for 5 min at 100° C. Samples were loaded onto the gels and electrophoresis was performed using a current of 30-50 mA and a potential difference of 125 V. After completion of electrophoresis the gels were fixed in destain (methanol/water/acetic acid (45:45:10, v/v) for three minutes at room temperature. For Coomassie blue staining, gels were placed in Coomassie brilliant blue (CBB) (0.2% w/v CBB R250, 30% v/v ethanol, 0.5% v/v acetic acid) and heated in a microwave until boiling and then allowed to cool for five minutes. The stain was removed and destain was added and heated in a microwave until boiling and allowed to cool for five minutes. Protein bands) were visualised by rinsing gels in Milli Q water overnight. A typical SDS-PAGE Coomassie blue stained gel of the Triton X114 extracted complex is shown in FIG. 2. Fourteen distinct bands (1 to 14) corresponding to approximate molecular masses of 75, 62, 57, 48, 45, 44, 39, 37, 34, 31, 27, 26, 17 and 15 kDa, respectively, were found. The proteins within these bands were identified using N-terminal sequencing and peptide mass fingerprinting techniques.

For N-terminal sequence analysis and Western blotting, proteins were transferred onto a PVDF membrane (Problott, Applied Biosystems) using a transblot cell (Bio-Rad). The PVDF membrane was wetted in 100% methanol and soaked in transfer buffer (10 mM CAPS, 10% v/v methanol, pH 11.5). Transfer was performed using a potential difference of 60 V for 90 min. For N-terminal sequencing membranes were stained with 0.1% (w/v) Coomassie brilliant blue R250 in methanol/water/acetic acid for 30 sec and destained in 50% v/v methanol. Protein bands were excised and N-terminal sequences determined using a Hewlett Packard 10005A protein sequencer. For peptide mass fingerprinting analysis; Coomassie blue stained protein bands from SDS-PAGE were excised and subjected to in-gel trypsin digestion and subsequent peptide extraction. Protein bands were excised from the Coomassie Blue stained SDS-PAGE gel and gel pieces were washed in 50 mM $NH_4HCO_3$/ethanol 1:1, reduced and alkylated with DTT and iodoacetamide, respectively and digested with sequencing grade modified trypsin (Promega) overnight at 37° C. as previously published Mortz et al. (1996). Electrophoresis 17:925-31]. The peptide extract containing 25 mM $NH_4HCO_3$ was then analysed by MALDI-TOF MS using an Ultraflex TOF/TOF instrument (Bruker Daltonics) in positive ion and reflectron mode. A saturated solution of 4-hydroxy-α-cyanocinnamic acid (HCCA) was prepared in 97:3 v/v acetone/0.1% v/v aqueous TFA. A thin layer was prepared by pipetting and immediately removing 2 μL, of this solution onto the 600 μm anchorchips of the target plate. Sample (0.5 μL) was deposited on the thin layers with 2.5 μL of 0.1% v/v aqueous TFA, and allowed to adsorb for 5 min, after which the sample solution was removed, and the thin layers washed once with 10 μL of ice-cold 0.1% v/v aqueous TFA for 1 min. Spectra were calibrated by close external calibration using a standard peptide mix. Proteins were identified by peptide mass fingerprinting against the *P. gingivalis* database (available from www.tigr.org) using an in-house Mascot search engine. Table 2 shows the peptide sequences used to identify the SDS-PAGE separated protein bands of the antigenic complex. The SDS-PAGE of the complex (FIG. 2) is annotated with the designation of the proteins identified by N-terminal sequencing and peptide mass fingerprinting. The complex was found to consist of: $Kgp_{cat}$, $RgpA_{cat}$, $RgpA_{A1}$, $Kgp_{A1}$, $RgpA_{A3}$, $RgpA_{A2}$, $Kgp_{A2}$, $HagA_{A1*}$, $HagA_{A1**}$, $HagA_{A3}$ and $HagA_{A2}$ as well as partially processed Kgp (residues 1 to 700 and residues 136 to 700). A schematic of the processed domains of RgpA, Kgp and HagA are shown in FIG. 3.

Figure 4:
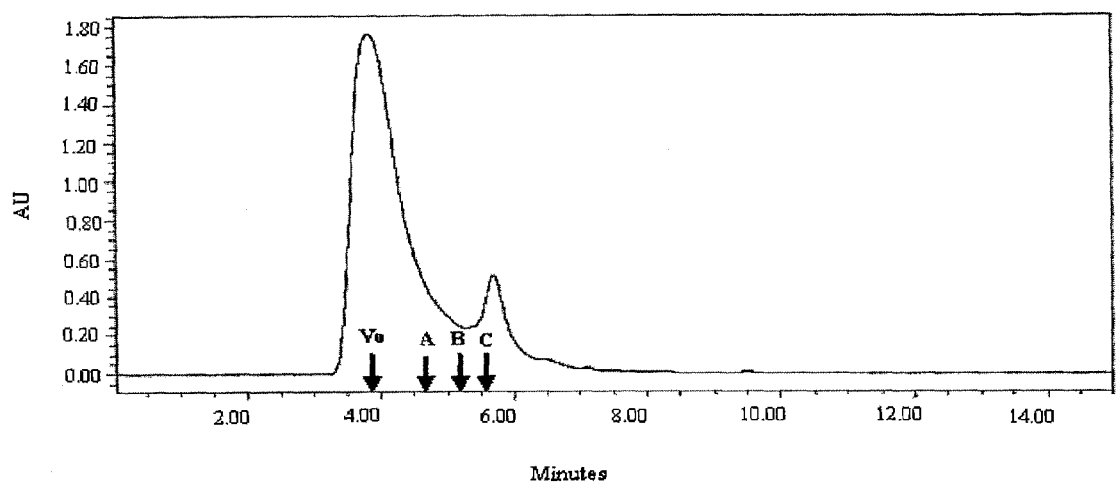
FIG. 4: Size exclusion chromatography of the Triton X114 extracted complex. Arginine-affinity purified Triton X114 extracted complex was applied to a size exclusion column (macrosphere 300 Å, 7 µm, 250×4.6 mm, Alltech, Australia). $V_0$ indicates the void volume of the column (Dextran Blue >2 million Da, was used to determine the void volume). The elution volumes of the standard proteins A=thyroglobulin (667 kDa), B=ferritin (440 kDa) and C=catalase (232 kDa) are marked.

The Triton X114 extracted complex was analysed by size exclusion chromatography. Size exclusion chromatography was performed using a macrosphere GPC 300 Å column (7 μm, 250×4.6 mm, with exclusion limits of 7,500-1,200,000 Daltons; Alltech, NSW, Australia) installed in a Waters Delta 600 HPLC system (Waters, Australia). Chromatography was performed at a flow rate of 0.5 mL/min in 0.05 M $KH_2PO_4$ containing 0.15 M $Na_2SO_4$ (pH 7.0). Material eluted from the column was detected by determining absorbance at 280 nm. A standard curve using molecular mass gel filtration standards (Amersham Pharmacia Biotech, Uppsala, Sweden) was used to determine the molecular mass of the eluted fractions. A typical size exclusion chromatogram of the purified Triton X114 extracted complex is shown in FIG. 4. The major peak (peak 1) eluted in the void volume of the column (>300 kDa; antigenic complex) and a second peak (peak 2) eluted with an average molecular mass of 223 kDa (the 223 kDa RgpA-Kgp complex).

TABLE 2

Identification Data for the proteins in the Arg-affinity purified Triton X114 extracted antigenic complex.

| Protein Band | Assigned designation | Identifying peptide | Observed mass |
|---|---|---|---|
| 1 | Kgp (42-700) | $^{42}$QFDASFSFNEVELTK$^{56}$ (SEQ ID No: 4) | 1761.86 |
| | | $^{61}$GGTFASVSIPGAFPTGEVGSPEVPAVRK$^{87}$ (SEQ ID No: 5) | 2286.3 |
| | | $^{88}$KLIAVPVGATPVVR$^{101}$ (SEQ ID No: 6) | 1419.93 |
| | | $^{89}$LIAVPVGATPVVR$^{101}$ (SEQ ID No: 7) | 1291.83 |
| | | $^{104}$SFTEQVYSLNQYGSEK$^{119}$ (SEQ ID No: 8) | 1879.89 |
| | | $^{130}$SDDPEKVPFVYNAAAYAR$^{147}$ (SEQ ID No: 9) | 2012.99 |
| | | $^{148}$KGFVGQELTQVEMLGTMR$^{165}$ (SEQ ID No: 10) | 2024.03 |
| | | $^{169}$IAALTINPVQYDVVANQLK$^{187}$ (SEQ ID No: 11) | 2070.17 |
| | | $^{190}$NNIEIEVSFQGADEVATQR$^{208}$ (SEQ ID No: 12) | 2120.03 |
| | | $^{209}$LYDASFSPYFETAYK$^{223}$ (SEQ ID No: 13) | 1801.85 |
| | | $^{229}$DVYTDHGDLYNTPVR$^{243}$ (SEQ ID No: 14) | 1764.84 |
| | | $^{254}$EALKPWLTWK$^{263}$ (SEQ ID No: 15) | 1271.73 |
| | | $^{267}$GFYLDVHYTDEAEVGTTNASIK$^{288}$ (SEQ ID No: 16) | 2430.15 |
| | | $^{295}$YNDGLAASAAPVFLALVGDTDVISGEK$^{321}$ (SEQ ID No: 17) | 2693.38 |
| | | $^{328}$VTDLYYSAVDGDYFPEMYTFR$^{348}$ (SEQ ID No: 18) | 2552.11 |
| | | $^{381}$VLLIAGADYSWNSQVGQPTIK$^{401}$ (SEQ ID No: 19) | 2260.21 |
| | | $^{402}$YGMQYYYNQEHGYTDVYNYLK$^{422}$ (SEQ ID No: 20) | 2712.18 |
| | | $^{602}$TNTYTLPASLPQNQASYSIQASAGSYVAISK$^{632}$ (SEQ ID No: 21) | 3231.66 |
| | | $^{633}$DGVLYGTGVANASGVATVSMTK$^{654}$ (SEQ ID No: 22) | 2098.07 |
| | | $^{655}$QITENGNYDVVITR$^{668}$ (SEQ ID No: 23) | 1621.83 |
| | | $^{677}$QIQVGEPSPYQPVSNLTATTQGQK$^{700}$ (SEQ ID No: 24) | 2571.31 |
| 2 | Kgp (136-700) | $^{136}$VPFVYNAAAYAR$^{147}$ (SEQ ID No: 25) | 1341.77 |
| | | $^{149}$GYVGQELTQVEMLGTMR$^{165}$ (SEQ ID No: 26) | 1896.02 |
| | | $^{169}$IAALTINPVQYDVVANQLK$^{187}$ (SEQ ID No: 11) | 2070.27 |
| | | $^{190}$NNIEIEVSFQGADEVATQR$^{208}$ (SEQ ID No: 12) | 2120.13 |
| | | $^{209}$LYDASFSPYFETAYK$^{223}$ (SEQ ID No: 13) | 1801.93 |
| | | $^{229}$DVYTDHGDLYNTPVR$^{243}$ (SEQ ID No: 14) | 1764.91 |
| | | $^{254}$EALKPWLTWK$^{263}$ (SEQ ID No: 15) | 1271.78 |
| | | $^{267}$GFYLDVHYTDEAEVGTTNASIK$^{288}$ (SEQ ID No: 16) | 2430.28 |
| | | $^{295}$YNDGLAASAAPVFLALVGDTDVISGEK$^{321}$ (SEQ ID No: 17) | 2693.54 |
| | | $^{328}$VTDLYYSAVDGDYFPEMYTFR$^{348}$ (SEQ ID No: 18) | 2552.25 |
| | | $^{349}$MSASSPEELTNIIDK$^{363}$ (SEQ ID No: 27) | 1634.88 |
| | | $^{381}$VLLIAGADYSWNSQVGQPTIK$^{401}$ (SEQ ID No: 19) | 2260.32 |
| | | $^{402}$YGMQYYYNQEHGYTDVYNYLK$^{422}$ (SEQ ID No: 20) | 2712.38 |
| | | $^{633}$DGVLYGTGVANASGVATVSMTK$^{654}$ (SEQ ID No: 22) | 2098.16 |
| | | $^{655}$QITENGNYDVVITR$^{668}$ (SEQ ID No: 23) | 1621.9 |
| | | $^{677}$QIQVGEPSPYQPVSNLTATTQGQK$^{700}$ (SEQ ID No: 24) | 2571.47 |

TABLE 2-continued

Identification Data for the proteins in the Arg-affinity purified Triton X114 extracted antigenic complex.

| Protein Band | Assigned designation | Identifying peptide | Observed mass |
|---|---|---|---|
| 3 | Kgp$_{cat}$ | $^{1}$DVYTDHGDLYNTPVR$^{15}$ (SEQ ID No: 14) | 1765.02 |
|  |  | $^{26}$EALKPWLTWK$^{35}$ (SEQ ID No: 15) | 1271.86 |
|  |  | $^{39}$GFYLDVHYTDEAEVGTTNASIK$^{60}$ (SEQ ID No: 16) | 2430.44 |
|  |  | $^{67}$YNDGLAASAAPVFLALVGDTDVISGEK$^{93}$ (SEQ ID No: 17) | 2693.71 |
|  |  | $^{100}$VTDLYYSAVDGDYFPEMYTFR$^{120}$ (SEQ ID No: 18) | 2552.43 |
|  |  | $^{125}$MSASSPEELTNIIDK$^{135}$ (SEQ ID No: 27) | 1635 |
|  |  | $^{153}$VLLIAGADYSWNSQVGQPTIK$^{173}$ (SEQ ID No: 19) | 2260.47 |
|  |  | $^{174}$YGMQYYYNQEHGYTDVYNYLK$^{194}$ (SEQ ID No: 20) | 2712.57 |
|  |  | $^{374}$TNTYTLPASLPQNQASYSIQASAGSYVAISK$^{404}$ (SEQ ID No: 21) | 3232.08 |
|  |  | $^{405}$DGVLYGTGVANASGVATVSMTK$^{426}$ (SEQ ID No: 22) | 2098.30 |
|  |  | $^{427}$QITENGNYDVVITR$^{440}$ (SEQ ID No: 23) | 1621.99 |
|  |  | $^{449}$QIQVGEPSPYQPVSNLTATTQGQK$^{472}$ (SEQ ID No: 24) | 2571.62 |
| 4 | RgpA$_{cat}$ | $^{228}$YTPVEEK$^{234}$ (SEQ ID No: 28) | 865.44 |
|  |  | $^{269}$VAEDIASPVTANAIQQFVK$^{287}$ (SEQ ID No: 29) | 2001.19 |
|  |  | $^{293}$EGNDLTYVLLIGDHK$^{307}$ (SEQ ID No: 30) | 1686.98 |
|  |  | $^{319}$SDQVYGQIVGNDHYNEVFIGR$^{339}$ (SEQ ID No: 31) | 2410.24 |
|  |  | $^{412}$CYDPGVTPK$^{420}$ (SEQ ID No: 32) | 1036.53 |
|  |  | $^{421}$NIIDAFNGGISLANYTGHGSETAWGTSHFGTTHVK$^{455}$ (SEQ ID No: 33) | 3661.11 |
|  |  | $^{493}$DGKPTGTVAIIASTINQSWASPMR$^{516}$ (SEQ ID No: 34) | 2501.4 |
|  |  | $^{517}$GQDEMNEILCEK$^{528}$ (SEQ ID No: 35) | 1465.73 |
|  |  | $^{536}$TFGGVTMNGMFAMVEK$^{551}$ (SEQ ID No: 36) | 1719.9 |
|  |  | $^{559}$MLDTWTVFGDPSLLVR$^{574}$ (SEQ ID No: 37) | 1850.06 |
| 5 | RgpA$_{A1}$ | $^{101}$IWIAGQGPTK$^{110}$ (SEQ ID No: 38) | 1070.69 |
|  |  | $^{122}$YHFLMKK$^{128}$ (SEQ ID No: 39) | 966 |
|  |  | $^{111}$EDDYVFEAGK$^{120}$ (SEQ ID No: 40) | 1172.62 |
|  |  | $^{129}$MGSGDGTELTISEGGGSDYTYTVYR$^{153}$ (SEQ ID No: 41) | 2616.31 |
|  |  | $^{160}$EGLTATTFEEDGVAAGNHEYCVEVK$^{184}$ (SEQ ID No: 42) | 2726.43 |
|  |  | $^{196}$DVTVEGSNEFAPVQNLTGSAVGQK$^{219}$ (SEQ ID No: 43) | 2447.39 |
| 6 | Kgp$_{A1}$ | $^{101}$MWIAGDGGNQpAR$^{113}$ (SEQ ID No: 44) | 1372.8 |
|  |  | $^{114}$YDDFTFEAGK$^{123}$ (SEQ ID No: 45) | 1192.65 |
|  |  | $^{114}$YDDFTFEAGKK$^{124}$ (SEQ ID No: 46) | 1320.77 |
|  |  | $^{124}$KYTFTMR$^{135}$ (SEQ ID No: 47) | 946.57 |
|  |  | $^{132}$AGMGDGTDMEVEDDSPASYTYTVYR$^{156}$ (SEQ ID No: 48) | 2730 |
|  |  | $^{161}$IKEGLTATTFEEDGVAAGNHEYCVEVK$^{187}$ (SEQ ID No: 49) | 2967.7 |
|  |  | $^{163}$EGLTATTFEEDGVAAGNHEYCVEVK$^{187}$ (SEQ ID No: 42) | 2726.54 |
|  |  | $^{199}$DVTVEGSNEFAPVQNLTGSSVGQK$^{222}$ (SEQ ID No: 43) | 2463.48 |
|  |  | $^{373}$GRIQGTWRQK$^{382}$ (SEQ ID No: 50) | 1230.6 |
| 7 | HagA$_{A1*/A1**}$ | $^{112}$HFGCTGIFR$^{120}$ (SEQ ID No: 51) (HagA$_{A1*}$ peptide confirmed by LIFT ms/ms) | 1094.56 |
|  |  | $^{95}$TIDLSAYAGQQVYLAFR$^{111}$ (SEQ ID No: 52) (HagA$_{A1*}$ sequence) | 1916.57 |
|  |  | $^{186}$DVTVEGSNEFAPVQNLTGSAVGQK$^{209}$ (SEQ ID No: 43) (HagA$_{A1*}$ sequence) | 2447.92 |
|  |  | $^{121}$LYLDDVAVSGEGSSNDYTYTVYR$^{143}$ (SEQ ID No: 53) (HagA$_{A1*}$ sequence) | 2587.85 |
|  |  | $^{820/1272}$PQSVWIER$^{827/1279}$ (SEQ ID No: 54) (HagA$_{A1**}$ sequence) | 1013.56 |
|  |  | $^{1079/1531}$TVVTAPEAIRGTR$^{1091/1543}$ (SEQ ID No: 55) (HagA$_{A1**}$ sequence) | 1370.73 |

TABLE 2-continued

Identification Data for the proteins in the Arg-affinity purified Triton X114 extracted antigenic complex.

| Protein Band | Assigned designation | Identifying peptide | Observed mass |
|---|---|---|---|
| 8 | RgpA$_{42}$/ Kgp$_{42}$/ HagA$_{42}$ | $^{100}$TGTNAGDFTVVFEETPNGIN$^{119}$ (SEQ ID No: 56) (2083) | 2083 |
|  |  | $^{80}$YYYAVNDGFPGDHYAVMISK$^{99}$ (SEQ ID No: 57) (2310) | 2310.23 |
| 9 | RgpA$_{43}$ | $^{1}$PQSVWIER$^{8}$ (SEQ ID No: 54) | 1014.59 |
|  |  | $^{63}$EGLTETTFEEDGVATGNHEYCVEVK$^{87}$ (SEQ ID No: 49) | 3055.65 |
|  |  | $^{97}$CVNVTVNSTQFNPVK$^{111}$ (SEQ ID No: 58) (confirmed BY LIFT ms/ms) | 1706.97 |
|  |  | $^{96}$KCVNVTVNSTQFNPVK$^{111}$ (SEQ ID No: 59) | 1835.09 |
|  |  | $^{63}$EGLTETTFEEDGVATGNHEYCVEVK$^{87}$ (SEQ ID No: 42) | 2814.46 |
|  | Kgp$_{43}$/HagA$_{43}$ | $^{1}$PQSVWIER$^{8}$ (SEQ ID No: 54) | 1014.59 |
|  |  | $^{63}$EGLTETTFEEDGVATGNHEYCVEVK$^{87}$ (SEQ ID No: 42) | 2814.46 |
|  |  | $^{61}$IKEGLTETTFEEDGVATGNHEYCVEVK$^{87}$ (SEQ ID No: 49) | 3055.65 |

(2) Preparation of Antibodies

Polyclonal antiserum to the complex was raised in mice by immunising with the O$_2$-inactivated complex subcutaneously. The mice were immunised at day 0 with 25 μg of protein in incomplete Freund's adjuvant and day 30 with 25 μg of protein in incomplete Freund's adjuvant. Immunisations were carried out using standard procedures. Polyclonal antisera having a high titre against P. gingivalis was obtained. If desired the antibodies directed specifically against P. gingivalis can be obtained using standard procedures.

Example 2

Methods and Compounds for Vaccine Formulations Related to Antigenic Complex

This embodiment of the present invention is to provide complex protein to be used in as an immunogen in a prophylactic and/or therapeutic vaccine for active immunisation to protect against or treat infections caused by P. gingivalis. For vaccine purposes, an antigen of P. gingivalis comprising a bacterial protein should be immunogenic, and induce functional antibodies directed to one or more surface-exposed epitopes on intact bacteria, wherein the epitope(s) are conserved amongst strains of P. gingivalis.

Protective Efficacy of Immunisation with the Antigenic Complex in Animal Models

The protective efficacy of the antigenic complex was evaluated in two internationally accepted animal models of P. gingivalis-infection i.e the lesion model and the periodontitis model. For the lesion model of disease, the maximum sizes of the lesions developed were statistically analyzed using the Kruskal-Wallis test and Mann-Whitney U-Wilcoxon rank sum test with a Bonferroni correction for type 1 error [Norusis M J (1993). SPPS for Windows: Base systems user's guide. Release 6.0 Chicago, Ill., USA: SPSS Inc]. For the periodontitis model, the bone loss (mm$^2$) data were statistically analyzed using One-Way analysis of variance and Dunnett's T3 test [Norusis M J (1993). SPPS for Windows: Base systems user's guide. Release 6.0 Chicago, Ill., USA: SPSS Inc].

Effect sizes, represented as Cohen's d were calculated using the effect size calculator provided on-line by Evidence-Based Education UK web site at http://www.cemcentre.org/ebeuk/research/effectsize/default.htm. According to Cohen [Cohen J (1969). Statistical Power Analysis for the Behavioural Sciences. New York: Academic Press] a small effect size is d≥0.2 and <0.5, moderate d≥0.5<0.8 and large d≥0.8

(1). Murine Lesion Model of P. gingivalis Infection

Figure 5:
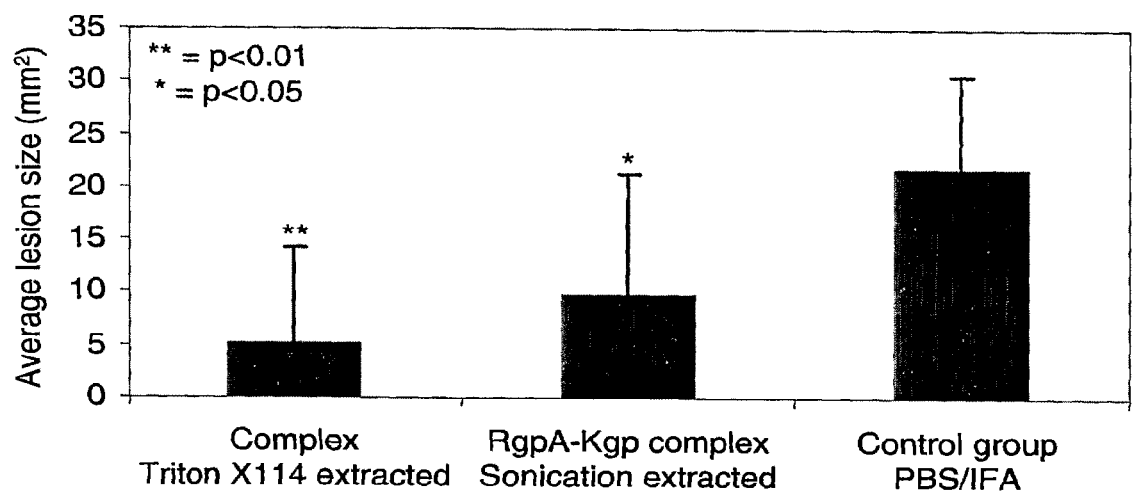
FIG. 5. Murine lesion model of *P. gingivalis* infection; average lesion size of mice immunized with antigenic complex extracted by sonication or by Triton X-114 methodologies. BALB/C mice (10 mice per group) were immunized subcutaneously (s.c.) with complex extracted by Triton X114 and sonication for the primary and secondary immunisations and challenged s.c. 12 days after the second immunisation with *P. gingivalis* ATCC 33277 ($1\times10^9$ viable cells). Animals were monitored over a period of 14 days for the development and size of lesions. Lesion sizes were statistically analyzed using Kruskal-Wallis test and Mann-Whitney U-Wilcoxon rank sum test with a Bonferroni correction for type 1 error. *, ** group significantly different ($p<0.05$, $p<0.01$, respectively) from the control (IFA/PBS) group.

This model is loosely based on the methods described by Kesavalu et al (1992) [Infect Immun 60:1455-1464]. A typical experiment is outlined below. The murine lesion model protocols were approved by the University of Melbourne Ethics Committee for Animal Experimentation. BALB/c mice 6-8 weeks old (10 mice/group) were immunized subcutaneously (scruff of the neck, 100 μL) with 25 μg of the Triton X114 extracted antigenic complex, 25 μg of sonication extracted RgpA-Kgp complex or phosphate buffered saline (pH 7.4) emulsified in Freund's adjuvant (IFA). After 30 days mice were boosted with antigen or PBS (subcutaneous injection, emulsified in IFA) and then 12 days later bled from the retrobulbar plexus. Two days after bleeding, mice were challenged with 7.5×10$^9$ viable cells of P. gingivalis strain ATCC 33277 by subcutaneous injection (100 μl) in the abdomen, and the lesions sizes measured over 14 days. The P. gingivalis inocula were prepared in PG buffer in the anaerobic workstation as described by O'Brien-Simpson et al [O'Brien-Simpson N et al. (2000). Infect Immun 68:4055-4063]. The number of viable cells in the inocula was verified by enumeration on horse blood agar plates. Lesion sizes were statistically analyzed using the Kruskal-Wallis test and the Mann-Whitney U-Wilcoxon rank sum test with a Bonferroni correction for type 1 error. The average lesion size of mice immunized with the antigenic complex extracted via Triton X114 or sonication was significantly (p<0.01; p<0.05, respectively) smaller than that of the PBS/IFA control group, indicating that immunization of mice with complex protects against P. gingivalis infection (FIG. 5). Furthermore, the Triton X114 extracted complex was more effective in protecting mice against P. gingivalis-induced lesions as indicated by the larger effect size of d=−1.85 (99.9% CI: −3.18, −0.32) compared to d=−1.32 (95% CI: −2.08, −0.10). Although, there was no significant difference in the lesion sizes of mice immunised with the Triton X114 or sonication extracted complex, the Triton X114 extracted complex when used as a vaccine was more effective in providing protection with an effect size of d=−0.42 (95% CI: −1.37, 0.49) compared to the sonication extracted complex. Moreover, only fifty percent of the mice immunised with the Triton X114 extracted complex developed *P. gingivalis*-induced lesions, whereas 70% of the mice immunised with sonication extracted complex developed lesions.

(2). Murine Periodontitis Model of *P. gingivalis* Infection

The murine periodontitis experiments were based on the model of Baker et al 1994 [Arch Oral Biol 39:1035-40] and were approved by the University of Melbourne Ethics Committee for Animal Experimentation. BALB/c mice 6-8 weeks old (10 mice per group) were immunized subcutaneously (s.c. 100 μL) with either 25 μg of the Triton X114 extracted complex or phosphate buffered saline (PBS), pH 7.4 emulsified in incomplete Freund's adjuvant (IFA). After 30 days the mice were boosted with antigen (s.c. injection, emulsified in IFA) and then bled 12 days later from the retrobulbar plexus. After bleeding mice received kanamycin (Sigma, New South Wales, Australia) at 1 mg/mL in deionised water ad libitum for 7 days. Three days after the antibiotic treatment mice were orally inoculated four times, two days apart with $1\times10^{10}$ viable *P. gingivalis* W50 cells (25 μL) in PG buffer containing 2% wt/vol carboxymethylcellulose (CMC, Sigma, New South Wales, Australia), a control group was sham-infected with PG buffer containing 2% wt/vol CMC alone. Two weeks later mice received another four doses (2 days apart) of $1\times10^{10}$ viable *P. gingivalis* W50 cells (25 μL) in PG buffer containing 2% wt/vol CMC. The number of viable cells in each inoculum was verified by enumeration on HB agar. Twenty-eight days after the second oral challenge mice were killed and the maxillae removed.

Figure 6:
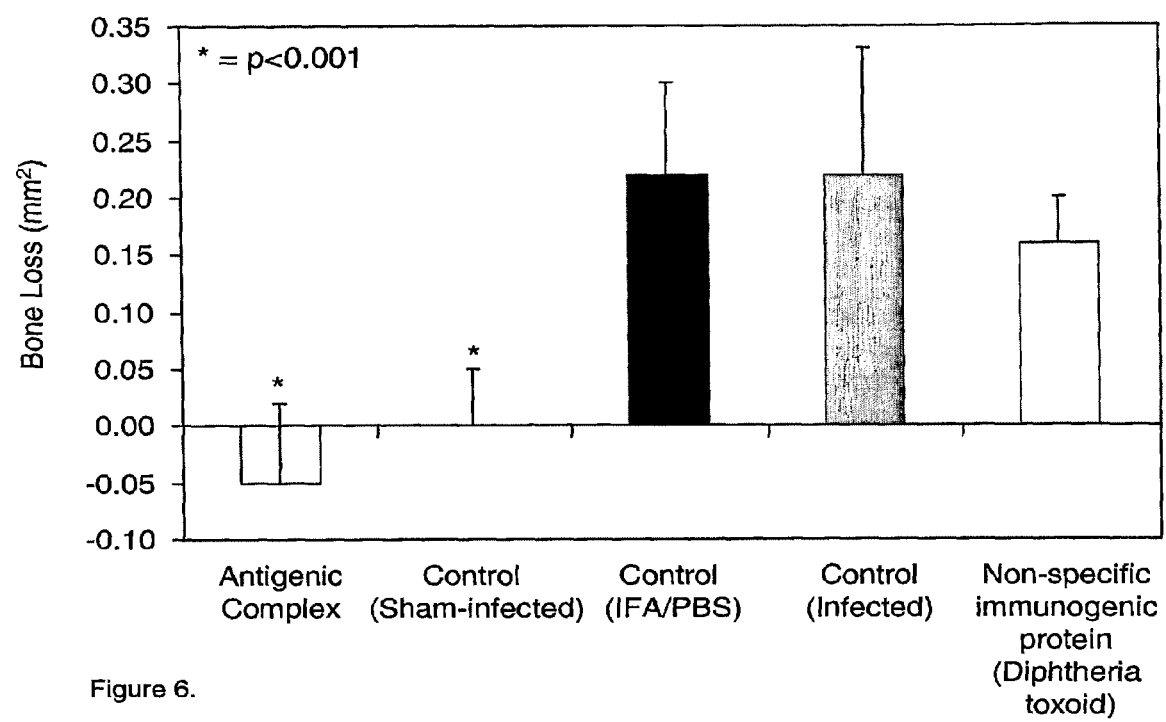
FIG. 6. Murine periodontitis model of *P. gingivalis*-induced periodontal bone loss. Periodontal bone loss of mice immunised with the Triton X114 extracted complex, non-specific immunogenic protein (diphtheria toxoid) and adjuvant alone (Control, IFA/PBS) or unimmunised orally infected (control, infected) mice. Measurement of bone loss is the mean area measured in mm2 from the cementoenamel junction (CEJ) to the alveolar bone crest (ABC) of the buccal side of each maxillary molar of both the left and right maxillae. Data was normally distributed as measured by Levene's homogeneity of variance and are presented as mean±SD (n=10) and were analyzed using the One-Way analysis of variance and Dunnett's T3 test and Cohen's Effect size. * group significantly different ($p<0.001$) from the orally infected control group and the orally infected control groups immunised with IFA/PBS or the non-specific immunogenic protein, diphtheria toxoid.

Maxillae were boiled (1 min) in deionised water, mechanically defleshed and immersed in 2% wt/vol potassium hydroxide (16 hours, 25° C.). The maxillae were then washed (2× deionised water) and immersed in 3% wt/vol hydrogen peroxide (6 hours, 25° C.). After washing (2×deionised water) the maxillae were stained with 0.1% wt/vol aqueous methylene blue and a digital image of the buccal side was captured with a Sound and Vision digital camera (Scitech Pty. Ltd, Melbourne, Australia) mounted on a dissecting microscope using Adobe Photoshop version 4.0 to assess horizontal bone loss. Horizontal bone loss is loss occurring in a horizontal plane, perpendicular to the alveolar bone crest that results in a reduction of the crest height. Maxillae were aligned so that the buccal and lingual molar cusps were superimposed. A micrometer scale in plane with the maxillae was digitally imaged at the same time so that measurements could be standardised for each image. The area from the cementoenamel junction (CEJ) to the alveolar bone crest (ABC) for each tooth was measured using Scion Image Beta 4.02 (Scion Corporation, Frederick, Md.) imaging software downloaded from the Scion Corporation website (http://www.scioncorp.com/index.htm). Bone loss measurements were determined twice in a random and blinded protocol by two standardised examiners. FIG. 6 shows that the Triton X114 extracted complex provided significant (p<0.001) protection from *P. gingivalis-induced* bone loss compared to control infected group, as well as, being significantly more effective (d=2.45, 99.9% CI: −4.73, −0.93) in providing protection against *P. gingivalis*-induced periodontitis compared to the non-specific highly immunogenic protein diphtheria toxoid.

These data show clearly that the antigenic complex extracted using the Triton X114 methodology is far superior to the sonication extraction method in providing protection against *P. gingivalis*-induced lesions and that the Triton X114 extracted complex also confers protection against bone loss in animal models of disease.

Example 3

Figure 7:
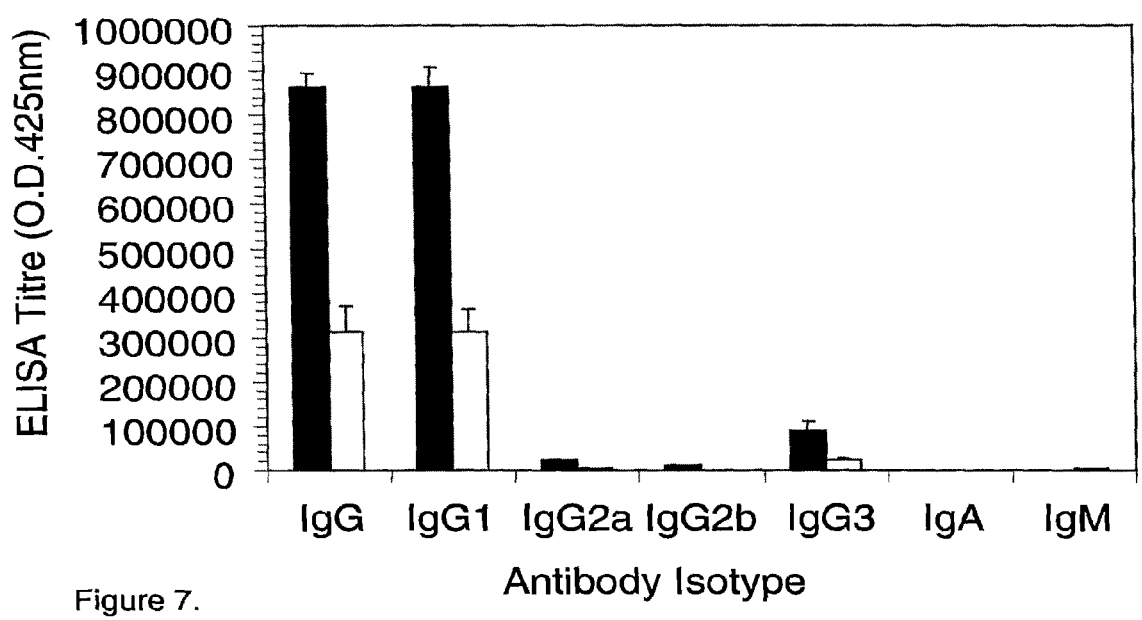
FIG. 7. Serum antibody subclass responses of immunised mice with the complex extracted using the Triton X114 and sonication methodologies. Sera from mice immunised with the Triton X114 (black bars) and sonication (white bars) extracted complex were used in the ELISA with the complex as the absorbed antigen. Antibody responses are expressed as the ELISA titre OD415 determined as the reciprocal of the dilution at which absorbance was double the background level, with each titre representing the mean±standard deviation of three values.

In one illustration of the antigenic complex having the properties desirable of a vaccine antigen, the protein was purified from *P. gingivalis* using the method described herein in Example 1. Mice were immunized with the purified inactivated Triton X114 and sonication extracted complex (25 μg) with adjuvant (IFA) two times at four week intervals. The purified complex was inactivated by air oxidation. Blood from the immunized mice was drawn 32 days after the last immunization and the immune sera were pooled. The pooled immune sera were assayed against the complex by an enzyme linked immunosorbent assay (ELISA) and a Western blot. ELISAs were performed in triplicate in wells of flat-bottom polyvinyl microtitre plates (Dynatech laboratories, McLean, Va.) coated with 10 μg/ml of *P. gingivalis* whole cells in 0.1 M phosphate-buffered saline (PBS), pH 7.4, overnight at 4° C. After removal of coating solution, 2% (w/v) skim milk powder in PBS, pH 7.4, containing 0.1% (v/v) Tween 20 was added to wells to block the uncoated plastic for 1 h at room temperature. After washing four times with PBS, pH 7.4 containing 0.1% v/v Tween 20 (PBST), serial dilutions of mouse sera in PBS, pH 7.4 containing 0.5% v/v skim milk (SK-PBS) were added to each well and incubated for 16 h at room temperature. After washing six times (PBST), a 1/2000 dilution of goat antisera to mouse IgM, IgA, IgG1, IgG2a, IgG2b, or IgG3 (Sigma, NSW, Australia) were added in SK-PBS and allowed to bind for 2 h at room temperature. Plates were washed six times (PBST) and a 1/5,000 dilution of horseradish peroxidase-conjugated rabbit anti-goat immunoglobulin in SK-PBS was added to each well. After washing (6 times, PBST), 100 μl of ABTS substrate [(0.9 mM 2,2′-azino-bis(3-ethylbenz-thiazoline-6) sulfonic acid) in 80 mM citric acid containing 0.005% (v/v) hydrogen peroxide, pH 4.0] was added to each well. The optical density at 415 nm (OD415) was measured using a BioRad microplate reader (BioRad microplate reader, model 450). ELISA titers were determined as the reciprocal of the dilution at which absorbance was double the background level, with each titer representing the mean±standard deviation of three values. The results, shown in FIG. 7, demonstrate that immunisation with inactivated complex extracted using the Triton X114 methodology elicit higher titer antibodies compared to the sonication extraction method. The Triton X114 extracted complex induced higher IgG, IgG1, IgG2a, IgG2b and IgG3 antibodies compared to the sonication extracted complex, with the predominant antibody being IgG1 (equivalent to IgG4 in humans), which has been shown to be the antibody that is involved in a protective immune response [O'Brien-Simpson et al. (2000). Infect Immun 68:4055-406; O'Brien-Simpson et al (2000) Infect Immun 68: 2704-2712].

Figure 8:
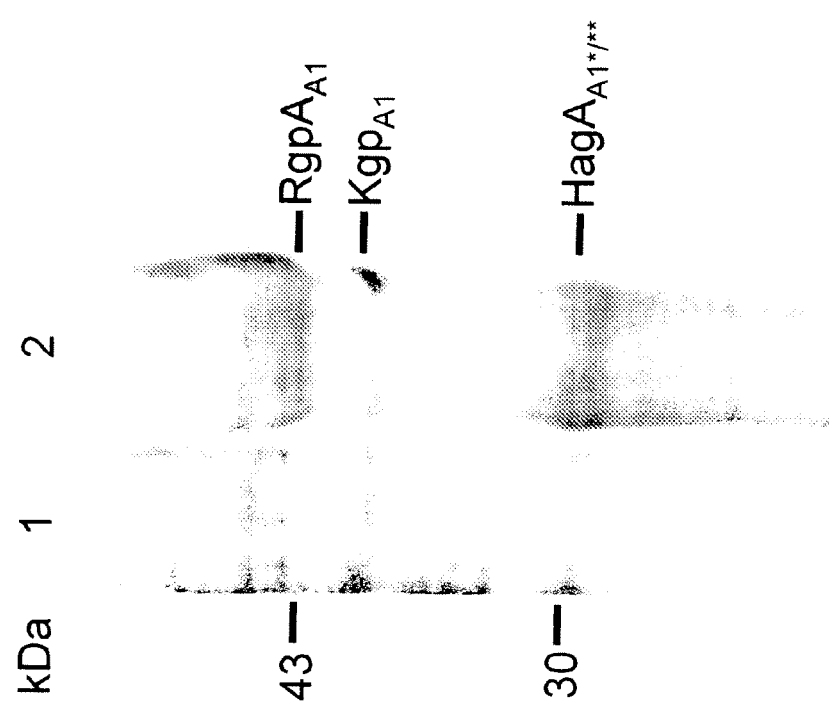
FIG. 8. Western blot analysis of the antigenic complex (Triton X114 extracted) and the RgpA-Kgp complex (sonication extracted) probed with antigenic complex or RgpA-Kgp complex antisera, respectively. The antigenic complex (Triton X114 extracted, lane 2) and RgpA-Kgp complex (sonication extracted, lane 1) were separated by SDS-PAGE, transferred onto PVDF membrane and probed with anti-complex antisera (1:50 TN buffer, lane 2), and anti-RgpA-Kgp complex antisera (1:50 TN buffer, lane 1). Molecular weight markers are shown in kilodaltons.

The purified Triton X114 extracted complex and the sonication extracted RgpA-Kgp complex were subjected to SDS-PAGE and electrophoretically transferred onto PVDF membrane as described above. After sectioning the membrane the molecular weight standards were stained) with 0.1% wt/vol CBB R250. The remaining sections were blocked for 1 hour at 20° C. with 5% wt/vol non-fat skim milk powder in TN buffer (50 mM Tris-HCl, pH 7.4, 100 mM NaCl). Sections were subsequently incubated with either anti-complex (Triton X114 extracted) antisera or anti-RgpA-Kgp complex (sonication extracted) antisera diluted 1:50 with TN buffer. After 16 hours at 20° C. the sections were washed (4×TN buffer containing 0.05% vol/vol Tween 20, 10 mins) and then incubated for an hour at 20° C. with horseradish peroxidase-conjugated goat immunoglobulin (Ig) directed against mouse Ig (1/400 dilution) (Sigma, NSW, Australia). After washing (4×TN buffer containing 0.05% vol/vol Tween 20, 10 mins) bound antibody was detected with 0.05% wt/vol 4-chloro-1-napthol in TN buffer containing 16.6% vol/vol methanol and 0.015% wt/vol $H_2O_2$. Colour development was stopped by rinsing the membranes with Milli D Q water. The anti-complex antisera (Triton X114 extracted) had a strong immunoreactive response to proteins of molecular weights 44, 39 and 30 kDa corresponding to the antigenic complex proteins RgpAA1, KgpA1 and HagAA1*/** (FIG. 8). The anti-RgpA-Kgp complex antisera (sonication extracted) also had a strong immunoreactive response to proteins of molecular weights 44, and 39 kDa corresponding to the antigenic complex proteins RgpAA1 and KgpA1 but had a very weak response to the HagAA1*/** adhesin (FIG. 8). The immunoreactive 45 kDa protein band was found not to be the RgpAcat proteinase domain as the complex antisera did not recognise the RgpB proteinase, which has 97% sequence identity to the RgpA proteinase, suggesting that the immunoreactive band detected at 45 kDa was also derived from the adhesins. These data indicate that the complex extracted using the Triton X114 method produces a strong antibody response directed towards the A1 adhesins of RgpA; Kgp and HagA polyproteins. These protein share a high degree of sequence similarity and each contain the previously described protective peptide epitopes ABM1, ABM2 and ABM3 (WO 98/49192). These results suggest that the large cell surface complexes on *P. gingivalis* are composed of non-covalently associated, processed domains of all three polyproteins, RgpA, Kgp and HagA. The superiority of the Triton X114-extracted complex in protection may, therefore, relate to the vaccine antigen more closely resembling the form of the proteins on the cell surface.

Additional evidence supporting the immunogenicity of the antigenic complex comes from a study of the human immune response in which 86% of 43 patients with adult periodontitis had specific IgG in their sera to the complex.

Example 4

The following is an example of a proposed toothpaste formulation containing anti-(complex) antibodies.

| Ingredient | % w/w |
| --- | --- |
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Chlorhexidine gluconate | 0.01 |
| Dextranase | 0.01 |
| Goat serum containing anti-Antigenic Complex antibodies | 0.2 |
| Water | balance |

Example 5

The following is an example of a proposed toothpaste formulation.

| Ingredient | % w/w |
| --- | --- |
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine serum containing anti-Antigenic Complex antibodies | 0.2 |
| Water | balance |

Example 6

The following is an example of a proposed toothpaste formulation.

| Ingredient | % w/w |
| --- | --- |
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine milk Ig containing anti-Antigenic Complex antibodies | 0.1 |
| Water | balance |

Example 7

The following is an example of a proposed toothpaste formulation.

| Ingredient | % w/w |
| --- | --- |
| Sorbitol | 22.0 |
| Irish moss | 1.0 |
| Sodium Hydroxide (50%) | 1.0 |
| Gantrez | 19.0 |
| Water (deionised) | 2.69 |
| Sodium Monofluorophosphate | 0.76 |
| Sodium saccharine | 0.3 |
| Pyrophosphate | 2.0 |
| Hydrated alumina | 48.0 |
| Flavour oil | 0.95 |
| anti-Antigenic Complex mouse monoclonal antibody | 0.3 |
| sodium lauryl sulphate | 2.00 |

Example 8

The following is an example of a proposed liquid toothpaste formulation.

| Ingredient | % w/w |
|---|---|
| Sodium polyacrylate | 50.0 |
| Sorbitol | 10.0 |
| Glycerol | 20.0 |
| Flavour | 1.0 |
| Sodium saccharin | 0.1 |
| Sodium monofluorophosphate | 0.3 |
| Chlorhexidine gluconate | 0.01 |
| Ethanol | 3.0 |
| Equine Ig containing anti-Antigenic Complex antibodies | 0.2 |
| Linolic acid | 0.05 |
| Water | balance |

Example 9

The following is an example of a proposed mouthwash formulation.

| Ingredient | % w/w |
|---|---|
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| Rabbit Ig containing anti-Antigenic Complex antibodies | 0.2 |
| Water | balance |

Example 10

The following is an example of a proposed mouthwash formulation.

| Ingredient | % w/w |
|---|---|
| Gantrez S-97 | 2.5 |
| Glycerine | 10.0 |
| Flavour oil | 0.4 |
| Sodium monofluorophosphate | 0.05 |
| Chlorhexidine gluconate | 0.01 |
| Lauroyl diethanolamide | 0.2 |
| Anti-Antigenic Complex mouse monoclonal antibody | 0.3 |
| Water | balance |

Example 11

The following is an example of a proposed lozenge formulation.

| Ingredient | % w/w |
|---|---|
| Sugar | 75-80 |
| Corn syrup | 1-20 |
| Flavour oil | 1-2 |
| NaF | 0.01-0.05 |
| Anti-Antigenic Complex mouse monoclonal antibody | 0.3 |
| Mg stearate | 1-5 |
| Water | balance |

Example 12

The following is an example of a proposed gingival massage cream formulation.

| Ingredient | % w/w |
|---|---|
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |
| Chlorhexidine gluconate | 0.1 |
| Anti-Antigenic Complex mouse monoclonal antibody | 0.3 |
| Water | balance |

Example 13

The following is an example of a proposed chewing gum formulation.

| Ingredient | % w/w |
|---|---|
| Gum base | 30.0 |
| Calcium carbonate | 2.0 |
| Crystalline sorbitol | 53.0 |
| Glycerine | 0.5 |
| Flavour oil | 0.1 |
| Anti-Antigenic Complex mouse monoclonal antibody | 0.3 |
| Water | balance |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A purified multimeric complex from *P. gingivalis*, the complex comprising proteins corresponding to at least one domain from each of RgpA, Kgp and HagA, and having a molecular weight greater than 300 kDa as determined by SDS page, wherein the purified multimeric complex comprises at least one domain from HagA that is HagA$_{A1*}$ (residues 366-625 of SEQ ID NO:3).

2. A complex according to claim 1 wherein the complex has a molecular weight greater than 500 kDa as determined by SDS page.

3. A complex according to claim 1 wherein the complex has a molecular weight greater than 800 kDa as determined by SDS page.

4. The complex according to claim 1 wherein an enzymatic activity of the complex is inactivated.

5. A composition for use in eliciting an immune response directed against *Porphyromonas gingivalis*, the composition comprising an effective amount of the complex according to claim 1 and a suitable adjuvant and/or acceptable carrier.

6. A method of reducing the severity of *Porphyromonas gingivalis* infection in an individual, the method comprising administering to the individual an amount of the composition according to claim 5 effective to induce an immune response in the individual directed against *Porphyromonas gingivalis*.

7. A method of treatment of a human or animal patient suffering from *Porphyromonas gingivalis* infection, the method comprising active vaccination of said patient with a composition according to the claim 5.

8. A method of raising an antibody, comprising immunizing an animal with the complex according to claim 1.

9. A method of eliciting an immune response directed against *Porphyromonas gingivalis*, comprising administering to an animal a composition comprising the complex according to claim 1 and a suitable adjuvant and/or acceptable carrier.

* * * * *